United States Patent [19]

Weidmann et al.

[11] Patent Number: 5,620,995

[45] Date of Patent: Apr. 15, 1997

[54] SUBSTITUTED HETEROCYCLIC CARBOXYAMIDES, THEIR PREPARATION AND THEIR USE AS PHARMACEUTICALS

[75] Inventors: Klaus Weidmann, Kronberg; Karl-Heinz Baringhaus, Wölfersheim; Georg Tschank, Klein-Winternheim; Martin Bickel, Bad Homburg, all of Germany

[73] Assignee: Hoechst Aktiengesellschaft, Frankfurt am Main, Germany

[21] Appl. No.: 365,411

[22] Filed: Dec. 28, 1994

[30] Foreign Application Priority Data

Dec. 30, 1993 [DE] Germany .............. 43 44 958.1
Nov. 9, 1994 [DE] Germany .............. 44 39 935.9

[51] Int. Cl.$^6$ ............ C07D 213/65; C07D 213/89; A61K 31/44
[52] U.S. Cl. .............. 514/350; 546/296; 546/298
[58] Field of Search ............... 546/296, 298; 514/350

[56] References Cited

U.S. PATENT DOCUMENTS 5,192,773  3/1993  Armistead et al. ............ 514/315
5,204,338  4/1993  Baader et al. ................ 514/183

FOREIGN PATENT DOCUMENTS

0562512A1  3/1993  European Pat. Off. .
0562512    9/1993  European Pat. Off. .

OTHER PUBLICATIONS

Gunhild Kaule et al., "Assay for 2-Oxoglutarate Decarboxylating Enzymes Based on the Determination of [1-14-C] Succinate: Application to Prolyl 4-Hydroxylase" Analytical Biochemistry, 184, pp. 291–297 (1990).

Georges Jolles, et al. "No. 354.—Pristinamycine. Synthé de L'heptapeptide Linéaire et d'oligopeptides correspondant au constituant IA de la Pristinamycine" Mémoires Présentés a la Société Chimique, pp. 2252–2259 (1965).

Search Report for EP94120766.4, 13 Apr. 1995.

G. Jolles, et al., Bulletin de la Societe Chimique ee France, No. 8, 1965, pp. 2252–2259, with CAS RN 3458-69-3 attachment.

R. J. Bergeron, et al., Journal of Medicinal Chemistry, vol. 37, No. 18, 1994, pp. 2889–2895.

Chemical Abstracts, vol. 115, No. 21, 1991, Abstract No. 222778s with attachment; CAS RN 136868-58-1 and CAS RN 136868-59-2.

Chemical Abstracts, vol. 95, No. 17, 1981, Abstract No. 151135k with attachment: CAS RN 77431-62-0, CAS RN 77421-44-0 and CAS RN 77421-43-3.

T. J. Franklin, *Biochem Soc Trans*, vol. 19(4), pp. 812–815, 1991.

R. J. Bergeron, *J Med Chem*, vol. 37, pp. 2889–2895, 1994.

*Primary Examiner*—C. Warren Ivy
*Assistant Examiner*—D. Margaret M. Mach
*Attorney, Agent, or Firm*—Finnegan, Henderson, Farabow, Garrett & Dunner, L.L.P.

[57] ABSTRACT

The invention relates to compounds of the formula I, to a process for their preparation and to their use as pharmaceuticals.

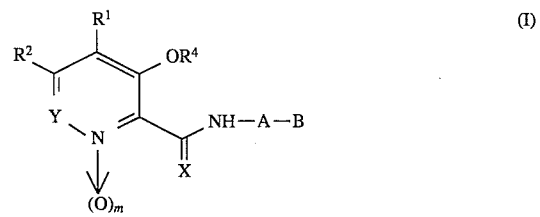

(I)

In particular, the compounds are used as inhibitors of prolyl-4-hydroxylase and as inhibitors of collagen biosynthesis, as pharmaceuticals against fibrotic diseases of the liver, the lung and the skin.

28 Claims, No Drawings

SUBSTITUTED HETEROCYCLIC CARBOXAMIDES, THEIR PREPARATION AND THEIR USE AS PHARMACEUTICALS

The invention relates to substituted heterocyclic carboxamides, to their preparation and to their use as inhibitors of prolyl-4-hydroxylase, and to their use as pharmaceuticals for treating fibrotic diseases.

Compounds which inhibit the enzymes proline hydroxylase and lysine hydroxylase bring about a very selective inhibition of collagen biosynthesis by their influence on the collagen-specific hydroxylation reactions. In the course of these reactions, protein-bound proline or lysine is hydroxylated by the enzymes proline hydroxylase or lysine hydroxylase, respectively. If this reaction is prevented by inhibitors, there then arises a non-functional, subhydroxylated collagen molecule which can only be secreted by the cells into the extracellular space in small quantities. Furthermore, the subhydroxylated collagen cannot be incorporated into the collagen matrix and is very readily degraded proteolytically. These effects result in a diminution of the overall quantity of collagen which is deposited extracellularly.

Inhibitors of prolyl hydroxylase are therefore suitable substances for use in the therapy of diseases in which the deposition of collagens makes a substantial contribution to the clinical picture. These diseases include, inter alia, fibroses of the lung, liver and skin (scleroderma and scars after burns, injuries and surgical operations) and also atherosclerosis.

It is known that the enzyme proline hydroxylase is efficiently inhibited by pyridine-2,4-dicarboxylic acid and pyridine-2,5-dicarboxylic acid (K. Majamaa et al., Eur. J. Biochem. 138 (1984) 239–245). However, these compounds are only active as inhibitors in cell culture at very high concentrations (Tschank, G. et al., Biochem. J. 238 (1987) 625 to 633). Prodrugs of pyridine-2,4(5)-dicarboxylates are also known. These are described in the relatively old German Applications P 42 33 124.2, P 42 38 506.7 and P 42 09 424.0.

N-Oxalylglycines which are inhibitors of prolyl-4-hydroxylase are disclosed in J. Med. Chem. 1992, 35, 2652 to 2658 (Cunliffe et al.), and EP-A-0 457 163 (Baader et al.).

3-Hydroxypyridine-2-carboxylic acid N-(carboxymethyl)amide is disclosed in G. Yolles et al. in: Bull. Soc. Chim. Fr. 1965, 8, 2252 to 2259.

Hydroxyisoquinolinecarboxylic acid glycylamides and hydroxycinnolinecarboxylic acid glycylamides are disclosed in Biochem. Soc. Trans. 1991, 19, 812 to 815 (Franklin et al.).

It has surprisingly now been found that heterocyclic carboxamides having an OH or SH function in the ortho-position to the amide function are highly effective inhibitors of prolyl-4-hydroxylase.

The compounds according to the invention conform to the formula I

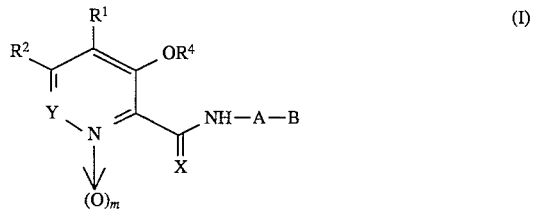

in which

Q is O or S,

X is O or S,

Y is N or $CR^3$, m is 0 or 1,

A is $(C_1-C_4)$-alkylene, which is optionally substituted by one or two substituents from the group halogen, cyano, nitro, trifluoromethyl, $(C_1-C_6)$-alkyl, $(C_1-C_6)$-hydroxyalkyl, $(C_1-C_6)$-alkoxy, —O—$[CH_2]_x$—$C_fH_{(2f+1-g)}Hal_g$, preferably $(C_1-C_8)$-fluoroalkoxy, $(C_1-C_8)$-fluoroalkenyloxy, $(C_1-C_8)$-fluoroalkynyloxy, —$OCF_2Cl$ or —O—$CF_2$—CHFCl, $(C_1-C_6)$-alkylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, N-$(C_1-C_4)$-alkylcarbamoyl, N,N-di-$(C_1-C_4)$-alkylcarbamoyl, $(C_1-C_6)$-alkyl-carbonyloxy, $(C_3-C_8)$-cycloalkyl, phenyl, benzyl, phenoxy, benzyloxy, anilino, N-methylanilino, phenylmercapto, phenylsulfonyl, phenylsulfinyl, sulfamoyl, N-$(C_1-C_4)$-alkylsulfamoyl or N,N-di-$(C_1-C_4)$-alkylsulfamoyl, or by a substituted $(C_6-C_{12})$-aryloxy, $(C_7-C_{11})$-aralkyloxy, $(C_6-C_{12})$-aryl or $(C_7-C_{11})$-aralkyl radical which carries in the aryl moiety 1, 2, 3, 4 or 5 identical or different substituents from the group halogen, cyano, nitro, trifluoromethyl, $(C_1-C_6)$-alkyl, $(C_1-C_6)$-alkoxy, —O—$[CH_2]_x$—$C_fH_{(2f+1-g)}Hal_g$, —$OCF_2Cl$, —O—$CF_2$—CHFCl, $(C_1-C_6)$-alkylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, N-$(C_1-C_4)$-alkylcarbamoyl, N,N-di-$(C_1-C_4)$-alkylcarbamoyl, $(C_1-C_6)$-alkylcarbonyloxy, $(C_3-C_8)$-cycloalkyl, sulfamoyl, N-$(C_1-C_4)$-alkylsulfamoyl or N,N-di-$(C_1-C_4)$-alkylsulfamoyl, or by the substituents $R^5$ of the α-carbon atom of an α-amino acid, it being possible to use the natural L-amino acids and their D-isomers;

B is an acid grouping from the group —$CO_2H$, —CONHCOR''', —CONHSOR''', —$CONHSO_2R'''$, —$NHSO_2CF_3$, tetrazolyl, imidazolyl or 3-hydroxyisoxazolyl, where R''' is aryl, heteroaryl, $(C_3-C_7)$-cycloalkyl or $(C_1-C_4)$-alkyl, optionally monosubstituted by $(C_6-C_{12})$-aryl, heteroaryl, OH, SH, $(C_1-C_4)$-alkyl, $(C_1-C_4)$-alkoxy, $(C_1-C_4)$-thioalkyl, $(C_1-C_4)$-sulfinyl, $(C_1-C_4)$-sulfonyl, $CF_3$, Cl, Br, F, I, $NO_2$, —COOH, $(C_2-C_5)$-alkoxycarbonyl, $NH_2$, mono-$(C_1-C_4$-alkyl)-amino, di-$(C_1-C_4$-alkyl)-amino or $(C_1-C_4)$-perfluoroalkyl, $R^1$, $R^2$ and $R^3$ are identical or different and are hydrogen, hydroxyl, halogen, cyano, trifluoromethyl, nitro, carboxyl, $(C_1-C_{20})$-alkyl, $(C_3-C_8)$-cycloalkyl, $(C_3-C_8)$-cycloalkyl-$(C_1-C_{12})$-alkyl, $(C_3-C_8)$-cycloalkoxy, $(C_3-C_8)$-cycloalkyl-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_8)$-alkyl-$(C_1-C_6)$-alkoxy, $(C_3-C_8)$-cycloalkyl-$(C_1-C_8)$-alkoxy-$(C_1-C_6)$-alkyl, $(C_3-C_8)$-cycloalkyloxy-$(C_1-C_8)$-alkoxy-$(C_1-C_6)$-alkyl, $(C_3-C_8)$-cycloalkoxy-$(C_1-C_8)$-alkoxy-$(C_1-C_8)$-alkoxy, $(C_6-C_{12})$-aryl, $(C_7-C_{16})$-aralkyl, $(C_7-C_{16})$-aralkenyl, $(C_7-C_{16})$-aralkynyl, $(C_2-C_{20})$-alkenyl, $(C_2-C_{20})$-alkynyl, $(C_1-C_{20})$-alkoxy, $(C_2-C_{20})$-alkenyloxy, $(C_2-C_{20})$-alkynyloxy, retinyloxy, $(C_1-C_{20})$-alkoxy-$(C_1-C_{12})$-alkyl, $(C_1-C_{12})$-alkoxy-$(C_1-C_{12})$-alkoxy, $(C_1-C_{12})$-alkoxy-$(C_1-C_8)$-alkoxy-$(C_1-C_8)$-alkyl, $(C_6-C_{12})$-aryloxy, $(C_7-C_{16})$-aralkyloxy, $(C_6-C_{12})$-aryloxy-$(C_1-C_6)$-alkoxy, $(C_7-C_{16})$-aralkoxy-$(C_1-C_6)$-alkoxy, $(C_1-C_{16})$-hydroxyalkyl, $(C_6-C_{16})$-aryloxy-$(C_1-C_8)$-alkyl, $(C_7-C_{16})$-aralkoxy-$(C_1-C_8)$-alkyl, $(C_6-C_{12})$-aryloxy-$(C_1-C_8)$-alkoxy-$(C_1-C_6)$-alkyl, $(C_7-C_{12})$-aralkyloxy- ($C_1$–$C_8$)-alkoxy-($C_1$–$C_6$)-alkyl, ($C_2$–$C_{20}$)-alkenyloxy-($C_1$–$C_6$)-alkyl, ($C_2$–$C_{20}$)-alkynyloxy-($C_1$–$C_6$)-alkyl, retinyloxy-($C_1$–$C_6$)-alkyl, —O—[CH$_2$—]$_x$—C$_f$H$_{(2f+1-g)}$F$_g$, —OCF$_2$Cl, —OCF$_2$—CHFCl, ($C_1$–$C_{20}$)-alkylcarbonyl, ($C_3$–$C_8$)-cycloalkylcarbonyl, ($C_6$–$C_{12}$)-arylcarbonyl, ($C_7$–$C_{16}$)-aralkylcarbonyl, cinnamoyl, ($C_2$–$C_{20}$)-alkenylcarbonyl, ($C_2$–$C_{20}$)-alkynylcarbonyl, ($C_1$–$C_{20}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkoxycarbonyl, ($C_3$–$C_8$)-cycloalkoxycarbonyl, ($C_2$–$C_{20}$)-alkenyloxycarbonyl, retinyloxycarbonyl ($C_2$–$C_{20}$)-alkynyloxycarbonyl, ($C_6$–$C_{12}$)-aryloxy-($C_1$–$C_6$)-alkoxycarbonyl, ($C_7$–$C_{16}$)-aralkoxy-($C_1$–$C_6$)-alkoxycarbonyl, ($C_3$–$C_8$)-cycloalkyl-($C_1$–$C_6$)-alkoxycarbonyl, ($C_3$–$C_8$)-cycloalkoxy-($C_1$–$C_6$)-alkoxycarbonyl, ($C_1$–$C_{12}$)-alkylcarbonyloxy, ($C_3$–$C_8$)-cycloalkylcarbonyloxy, ($C_6$–$C_{12}$)-arylcarbonyloxy, ($C_7$–$C_{16}$)-aralkylcarbonyloxy, cinnamoyloxy, ($C_2$–$C_{12}$)-alkenylcarbonyloxy, ($C_2$–$C_{12}$)-alkynylcarbonyloxy, ($C_1$–$C_{12}$)-alkoxycarbonyloxy, ($C_1$–$C_{12}$)-alkoxy-($C_1$–$C_{12}$)-alkoxycarbonyloxy, ($C_6$–$C_{12}$)-aryloxycarbonyloxy, ($C_7$–$C_{16}$)-aralkyloxycarbonyloxy, ($C_3$–$C_8$)-cycloalkoxycarbonyloxy, ($C_2$–$C_{12}$)-alkenyloxycarbonyloxy, ($C_2$–$C_{12}$)-alkynyloxycarbonyloxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N,N-dicyclo-($C_3$–$C_8$)-alkylcarbamoyl, N-($C_1$–$C_{10}$)-alkyl-N-($C_3$–$C_8$)-cycloalkylcarbamoyl, N-(($C_3$–$C_8$)-cycloalkyl-($C_1$–$C_6$)-alkyl)carbamoyl, N-($C_1$–$C_6$)-alkyl-N-(($C_3$–$C_8$)-cycloalkyl-($C_1$–$C_6$)-alkyl)carbamoyl, N-(+)-dehydroabietylcarbamoyl, N-($C_1$–$C_6$)-alkyl-N-(+)-dehydroabietylcarbamoyl, N-($C_6$–$C_{12}$)-arylcarbamoyl, N-($C_7$–$C_{16}$)-aralkylcarbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N-(($C_1$–$C_{18}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-(($C_1$–$C_{10}$)-alkoxy-($C_1$–$C_{10}$)-alkyl)carbamoyl, N-($C_1$–$C_{10}$)-alkyl-N-(($C_6$–$C_{12}$)-aryloxy-($C_1$–$C_{10}$)-8alkyl)carbamoyl, N-($C_1$–$C_{10}$)-alkyl-N-(($C_7$–$C_{16}$)-aralkyloxy-($C_1$–$C_{10}$)-alkyl)carbamoyl, or CON(CH$_2$)$_h$, in which a CH$_2$ group can be replaced by O, S, N-($C_1$–$C_8$)-alkylimino, N-($C_3$–$C_8$)-cycloalkylimino, N-($C_3$–$C_8$)-cycloalkyl-($C_1$–$C_4$)-alkylimino, N-($C_6$–$C_{12}$)-arylimino, N-($C_7$–$C_{16}$)-aralkylimino or N-($C_1$–$C_4$)-alkoxy-($C_1$–$C_6$)-alkylimino, and h is from 3 to 7, a carbamoyl radical of the formula J

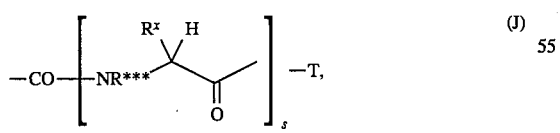

in which $R^x$ is the substituent of an α-amino acid, including the L and D amino acids, s is 1, 2, 3, 4 or 5, and T is OH, OR or NR*R**, where R*, R and R* are identical or different and are hydrogen, ($C_6$–$C_{12}$)-aryl, ($C_7$–$C_{11}$)-aralkyl, ($C_1$–$C_8$)-alkyl, ($C_3$–$C_8$)-cycloalkyl, (+)-dehydroabietyl, ($C_1$–$C_8$)-alkoxy-($C_1$–$C_8$)-alkyl, ($C_7$–$C_{12}$)-aralkoxy-($C_1$–$C_8$)-alkyl, ($C_6$–$C_{12}$)-aryloxy-($C_1$–$C_8$)-alkyl, ($C_1$–$C_{10}$)-alkanoyl, optionally substituted ($C_7$–$C_{16}$)-aralkanoyl or optionally substituted ($C_6$–$C_{12}$)-aroyl, or R* and R** are together -[CH$_2$]$_h$, in which a CH$_2$ group can be replaced by O, S, SO, SO$_2$, N-acylamino, N-($C_{1-C10}$)-alkoxycarbonylimino, N-($C_1$–$C_8$)-alkylimino, N-($C_3$–$C_8$)-cycloalkylimino, N-($C_3$–$C_8$)-cycloalkyl-($C_1$–$C_4$)-alkylimino, N-($C_6$–$C_{12}$)-arylimino, N-($C_7$–$C_{16}$)-aralkylimino or N-($C_1$–$C_4$)-alkoxy-($C_1$–$C_6$)-alkylimino and h is from 3 to 7, carbamoyloxy, N-($C_1$–$C_{12}$)-alkylcarbamoyloxy, N,N-di-($C_1$–$C_{12}$)-alkylcarbamoyloxy, N-($C_3$–$C_8$)-cycloalkylcarbamoyloxy, N-($C_6$–$C_{12}$)-arylcarbamoyloxy, N-($C_7$–$C_{16}$)aralkylcarbamoyloxy, N-($C_1$–$C_{10}$)-alkyl-N-($C_6$–$C_{12}$)-arylcarbamoyloxy, N-($C_1$–$C_{10}$)-alkyl-N-($C_7$–$C_{16}$)-aralkylcarbamoyloxy, N-(($C_1$–$C_{10}$)-alkyl)carbamoyloxy, N-(($C_6$–$C_{12}$)-aryloxy-($C_1$–$C_{10}$)-alkyl)carbamoyloxy, N-(($C_7$–$C_{16}$)-aralkyloxy-($C_1$–$C_{10}$)-alkyl)carbamoyloxy, N-($C_1$–$C_{10}$)-alkyl-N-(($C_1$–$C_{10}$)-alkoxy-($C_1$–$C_{10}$)-alkyl)-carbamoyloxy, N-($C_1$–$C_{10}$)-alkyl-N-(($C_6$–$C_{12}$)-aryloxy-($C_1$–$C_{10}$)-alkyl)carbamoyloxy, N-($C_1$–$C_{10}$)-alkyl-N-(($C_7$–$C_{16}$)-aralkyloxy-($C_1$–$C_{10}$)-alkyl)carbamoyloxy, amino, ($C_1$–$C_{12}$)-alkylamino, di-($C_1$–$C_{12}$)-alkylamino, ($C_3$–$C_8$)-cycloalkylamino, ($C_3$–$C_{12}$)-alkenylamino, ($C_3$–$C_{12}$)-alkynylamino, N-($C_6$–$C_{12}$)-arylamino, N-($C_7$–$C_{11}$)-aralkylamino, N-alkyl-aralkylamino, N-alkyl-arylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroylN-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_8$)-alkyl, ($C_3$–$C_8$)-cycloalkanoylamino-($C_1$–$C_8$)-alkyl, ($C_6$–$C_{12}$)-aroylamino-($C_1$–$C_8$)-alkyl, ($C_7$–$C_{16}$)-aralkanoylamino-($C_{1-C8}$)-alkyl, amino-($C_1$–$C_{10}$)-alkyl, N-($C_1$–$C_{10}$)-alkylamino-($C_1$–$C_{10}$)-alkyl, N,N-di-($C_1$–$C_{10}$)-alkylamino-($C_1$–$C_{10}$)-alkyl, ($C_3$–$C_8$)-cycloalkylamino-($C_1$–$C_{10}$)-alkyl, ($C_1$–$C_{20}$)-alkyl-mercapto, ($C_1$–$C_{20}$)-alkylsulfinyl, ($C_1$–$C_{20}$)-alkylsulfonyl, ($C_6$–$C_{12}$)-arylmercapto, ($C_6$–$C_{12}$)-arylsulfinyl, ($C_6$–$C_{12}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, ($C_1$–$C_{12}$)-alkylmercapto-($C_1$–$C_6$)-alkyl, ($C_1$–$C_{12}$)-alkylsulfinyl-($C_1$–$C_6$)-alkyl, ($C_1$–$C_{12}$)-alkysulfonyl-($C_1$–$C_6$)-alkyl, ($C_6$–$C_{12}$)-arylmercapto-($C_1$–$C_6$)-alkyl, ($C_6$–$C_{12}$)-arylsulfinyl-($C_1$–$C_6$)-alkyl, ($C_6$–$C_{12}$)-arylsulfonyl-($C_1$–$C_6$)-alkyl, ($C_7$–$C_{16}$)-aralkylmercapto-($C_1$–$C_6$)-alkyl, ($C_7$–$C_{16}$)-aralkylsulfinyl-($C_1$–$C_6$)-alkyl, ($C_7$–$C_{16}$)-aralkylsulfonyl-($C_1$–$C_6$)-alkyl, sulfamoyl, N-($C_1$–$C_{10}$)-alkylsulfamoyl, N,N-di-($C_1$–$C_{10}$)-alkylsulfamoyl, ($C_3$–$C_8$)-cycloalkylsulfamoyl, N-($C_6$–$C_{12}$)-arylsulfamoyl, N-($C_7$–$C_{16}$)-aralkylsulfamoyl, N-($C_1$–$C_{10}$)-alkyl-N-($C_6$–$C_{12}$)-arylsulfamoyl, N-($C_1$–$C_{10}$)-alkyl-N-($C_7$–$C_{16}$)-aralkylsulfamoyl, ($C_1$–$C_{10}$)-alkylsulfonamido, N-(($C_1$–$C_{10}$)-alkyl)-($C_1$–$C_{10}$)-alkylsulfonamido, ($C_7$–$C_{16}$)-aralkylsulfonamido or N-(($C_1$–$C_{10}$)-alkyl)-($C_7$–$C_{16}$)-aralkylsulfonamido, where the radicals which contain an aryl radical can, for their part, be substituted on the aryl by from 1 to 5 identical or different radicals from the group:

hydroxyl, halogen, cyano, trifluoromethyl, nitro, carboxyl, $(C_1-C_{16})$-alkyl, $(C_3-C_8)$-cycloalkyl, $(C_3-C_8)$-cycloalkyl-$(C_1-C_{12})$-alkyl, $(C_3-C_8)$-cycloalkoxy, $(C_3-C_8)$-cycloalkoxy-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_8)$-alkyl-$(C_1-C_6)$-alkoxy, $(C_3-C_8)$-cycloalkyl-$(C_1-C_8)$-alkoxy-$(C_1-C_6)$-alkyl, $(C_3-C_8)$-cycloalkoxy-$(C_1-C_8)$-alkoxy-$(C_1-C_8)$-alkoxy, $(C_3-C_8)$-cycloalkoxy-$(C_1-C_8)$-alkoxy-$(C_1-C_6)$-alkyl, $(C_6-C_{12})$-aryl, $(C_7-C_{16})$-aralkyl, $(C_2-C_{16})$-alkenyl, $(C_2-C_{12})$-alkynyl, $(C_1-C_6)$-alkoxy, $(C_1-C_{16})$-alkenyloxy, $(C_1-C_{12})$-alkoxy-$(C_1-C_{12})$-alkyl, $(C_1-C_{12})$-alkoxy-$(C_1-C_{12})$-alkoxy, $(C_1-C_{12})$-alkoxy-$(C_1-C_8)$-alkoxy-$(C_1-C_8)$-alkyl, $(C_6-C_{12})$-aryloxy, $(C_7-C_{16})$-aralkyloxy, $(C_6-C_{12})$-aryloxy-$(C_1-C_6)$-alkoxy, $(C_7-C_{16})$-aralkyloxy-$(C_1-C_6)$-alkoxy, $(C_1-C_8)$-hydroxyalkyl, $(C_6-C_{16})$-aryloxy-$(C_1-C_8)$-alkyl, $(C_7-C_{16})$-aralkyloxy-$(C_1-C_8)$-alkyl, $(C_6-C_{12})$-aryloxy-$(C_1-C_8)$-alkoxy-$(C_1-C_6)$-alkyl, $(C_7-C_{12})$-aralkyloxy-$(C_1-C_8)$-alkoxy-$(C_1-C_6)$-alkyl, —O—[CH$_2$-]$_x$—C$_f$H$_{(2f+1-g)}$F$_g$, —OCF$_2$Cl, —OCF$_2$—CHFCl, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{12})$-alkenyloxycarbonyl, $(C_2-C_{12})$-alkynyloxycarbonyl, $(C_6-C_{12})$-aryloxy-$(C_1-C_6)$-alkoxycarbonyl, $(C_7-C_{16})$-aralkoxy-$(C_1-C_6)$-alkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkenyloxycarbonyloxy, $(C_2-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N,N-dicyclo-$(C_3-C_8)$-alkylcarbamoyl, N-$(C_1-C_{10})$-alkyl-N-$(C_3-C_8)$-cycloalkylcarbamoyl, N-(($C_3-C_8$)-cycloalkyl-$(C_1-C_6)$-alkyl)carbamoyl, N-$(C_1-C_6)$-alkyl-N-(($C_3-C_8$)-cycloalkyl-$(C_1-C_6)$-alkyl)carbamoyl, N-(+)-dehydroabietylcarbamoyl, N-$(C_1-C_6)$-alkyl-N-(+)-dehydroa-bietyl-carbamoyl, N-$(C_6-C_{12})$-arylcarbamoyl, N-$(C_7-C_{16})$-aralkylcarbamoyl, N-$(C_1-C_{10})$-alkyl-N-$(C_6-C_{16})$arylcarbamoyl, N-$(C_1-C_{10})$-alkyl-N-$(C_7-C_{16})$-aralkylcarbamoyl, N-(($C_1-C_{16}$)-alkoxy-$(C_1-C_{10})$-alkyl)-carbamoyl, N(($C_6-C_{16}$)-aryloxy-$(C_1-C_{10})$alkyl)carbamoyl, N-(($C_7-C_{16}$)-aralkyloxy-$(C_1-C_{10})$alkyl)carbamoyl, N-$(C_1-C_{10})$-alkyl-N-(($C_1-C_{10}$)-alkoxy-$(C_1-C_{10})$alkyl)carbamoyl, N-$(C_1-C_{10})$-alkyl-N-(($C_6-C_{12}$)-aryloxy-$(C_1-C_{10})$alkyl)carbamoyl, N-$(C_1-C_{10})$-alkyl-N-(($C_7-C_{16}$)-aralkyloxy-$(C_1-C_{10})$-alkyl)carbamoyl or CON(CH$_2$)$_h$ in which a CH$_2$ group can be replaced by O, S, N-$(C_1-C_8)$-alkylimino, N-$(C_3-C_8)$-cycloalkylimino, N-$(C_3-C_8)$-cycloalkyl-$(C_1-C_4)$alkylimino, N-$(C_6-C_{12})$-arylimino, N-$(C_7-C_{16})$-aralkylimino or N-$(C_1-C_4)$-alkoxy-$(C_1-C_6)$-alkylimino, and h is from 3 to 7, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{12})$arylcarbamoyloxy, N-$(C_1-C_{10})$-alkyl-N-$(C_7-C_{16})$-aralkylcarbamoyloxy,
N-(($C_1-C_{10}$)alkyl)carbamoyloxy, N-(($C_6-C_{12}$)-aryloxy-$(C_1-C_{10})$alkyl)carbamoyloxy, N-(($C_7-C_{16}$)-aralkyloxy-$(C_1-C_{10})$alkyl)carbamoyloxy, N-$(C_1-C_{10})$-alkyl-N-(($C_1-C_{10}$)-alkoxy-$(C_1-C_{10})$alkyl)carbamoyloxy, N-$(C_1-C_{10})$-alkyl-N-(($C_6-C_{12}$)-aryloxy-$(C_1-C_{10})$alkyl)carbamoyloxy, N-$(C_1-C_{10})$-alkyl-N-(($C_7-C_{16}$)-aralkyloxy-$(C_1-C_{10})$-alkyl)carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-alkyl-aralkylamino, N-alkyl-arylamino, $(C_1-C_{12})$-alkoxyamino, $(C_1-C_{12})$-alkoxy-N-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{12})$-aroylamino-$(C_1-C_8)$-alkyl, $(C_7-C_{16})$-aralkanoylamino-$(C_1-C_8)$-alkyl, amino-$(C_1-C_{10})$-alkyl,N-$(C_1-C_{10})$alkylamino-$(C_1-C_{10})$alkyl,N,N-di-$(C_1-C_{10})$alkylamino-$(C_1-C_{10})$alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl or $(C_7-C_{16})$-aralkylsulfonyl, R$^1$ and R$^2$ or R$^2$ and R$^3$ form a chain [CH$_2$]$_o$ in which one or two CH$_2$ groups of the saturated chain or the chain unsaturated with a C=C double bond are, where appropriate, replaced by O, S, SO, SO$_2$ or NR', o is 3, 4 or 5, and R' is hydrogen, $(C_6-C_{12})$-aryl, $(C_1-C_8)$-alkyl, $(C_1-C_8)$-alkoxy-$(C_1-C_8)$-alkyl, $(C_7-C_{12})$-aralkoxy-$(C_1-C_8)$-alkyl, $C_6-C_{12})$-aryloxy-$(C_1-C_8)$-alkyl, $(C_1-C_{10})$-alkanoyl, optionally substituted $(C_7-C_{16})$-aralkanoyl or optionally substituted $(C_6-C_{12})$-aroyl, where the radicals R$^1$ and R$^2$ or R$^2$ and R$^3$, together with the pyridine or pyridazine carrying them, preferably form a 5, 6, 7, 8-tetrahydroisoquinoline ring, a 5, 6, 7, 8-tetrahydroquinoline ring or a 5, 6, 7, 8-tetrahydrocinnoline ring, or R$^2$ and R$^3$ form a carbocyclic or a heterocyclic, 5- or 6-membered aromatic ring, where the radicals R$^2$ and R$^3$, together with the pyridine or pyridazine carrying them, preferably form the following optionally substituted heterocyclic ring systems:
thienopyridines,
furanopyridines,
pyridopyridines,
pyrimidinopyridines,
imidazopyridines,
thiazolopyridines,
oxazolopyridines, and
quinolines, where quinolines preferably satisfy the Formula 1a $$\text{(1a)}$$

and the substituents $R^{13}$ to $R^{16}$, in each case independently of each other, have the meaning of $R^1$, $R^2$ and $R^3$, $R^4$ is hydrogen, and f is 1 to 8, g is 0 or 1 to (2f+1), x is 0 to 3 and h is 3 to 6, including the physiologically active salts, with 3-hydroxypyridine-2-carboxylic acid N-(carboxymethyl)amide being excepted.

Aryl is understood to mean, in particular, phenyl and naphthyl, heteroaryl is understood to mean, in particular, pyridyl, picolyl or thienylmethyl, cycloalkyl is understood to mean, preferably, cyclohexyl, and halogen is understood to mean, in particular, fluorine, chlorine and bromine.

The invention also embraces salts of the compounds of the formula I.

The formation of salts with basic reagents can take place once or twice on the acidic groups of the compounds of the formula I, i.e. on the radicals B, $R^1$, $R^2$ and $R^3$, and/or on the acidic phenolic OH(SH) group, in particular on the radicals B and $R^2$ and the phenolic OH(SH) group.

Examples of reagents being used are alcoholates, hydroxides, carbonates, hydrogen carbonates, hydrogen phosphates, organometallic compounds of the alkali and alkaline earth elements, the elements of the 3rd and 4th main groups of the Periodic System, and the elements of the transition metals, amines, optionally substituted 1 to 3 times by $(C_1-C_8)$-hydroxyalkyl, $(C_1-C_4)$-alkoxy-$(C_1-C_8)$-alkyl, phenyl, benzyl or $(C_1-C_8)$-alkyl, which can be substituted 1 to 3 times by hydroxyl or $(C_1-C_4)$-alkoxy, for example tromethane, (Tris buffer), 2-aminoethanol, 3-aminopropanol, hydroxylamine, dimethylhydroxylamine, 2-methoxyethylamine, 3-ethoxypropylamine, and basic amino acids and amino acid derivatives, such as amino acid esters, histidine, arginine and lysine, and their derivatives, and also pharmaceuticals which contain a basic group, such as, for example, ®Amiloride, ®Verapamil and beta blockers.

The invention also relates to the compounds according to formula I, plus 3-hydroxypyridine-2-carboxylic acid N-(carboxymethyl)amide for use as pharmaceuticals.

Compounds of the formula I are of particular importance in which

Q is O or S,

X is O,

Y is $CR^3$, m is 0 and 1,

A is $(C_1-C_3)$-alkylene, which is optionally substituted once by halogen, cyano, trifluoromethyl, $(C_1-C_6)$-alkyl, $(C_1-C_6)$-hydroxyalkyl, $(C_1-C_6)$-alkoxy or —O—$[CH_2]_x$—$C_fH_{(2f+1-g)}F_g$, or A is —$CHR^5$—, . where $R^5$ is one of the substituents of the α-carbon atom of an α-amino acid, in particular of a natural L-amino acid and of its D-isomer, B is $CO_2H$, $R^2$ is hydrogen, $(C_1-C_{20})$-alkyl, $(C_2-C_{20})$-alkenyl, $(C_2-C_{20})$-alkynyl, $(C_1-C_{20})$-alkoxy, $(C_2-C_{20})$-alkenyloxy, $(C_2-C_{20})$-alkynyloxy, retinyloxy, $(C_1-C_{20})$-alkoxy-$(C_1-C_3)$-alkyl, $(C_2-C_{20})$-alkenyloxy-$(C_1-C_3)$-alkyl, retinyloxy-$(C_1-C_3)$-alkyl, $(C_2-C_{20})$-alkynyloxy-$(C_1-C_3)$-alkyl, halogen, cyano, trifluoromethyl, $(C_1-C_8)$-hydroxyalkyl, $(C_1-C_{20})$-alkanoyl, $(C_7-C_{16})$-aralkanoyl, $(C_6-C_{12})$-aroyl, $(C_6-C_{12})$-aryl, $(C_7-C_{16})$-aralkyl, —O—$[CH_2]_x$—$C_fH_{(2f+1-g)}F_g$, NR'R", $(C_1-C_{10})$-alkylmercapto, $(C_1-C_{10})$-alkylsulfinyl, $(C_1-C_{10})$-alkylsulfonyl, $(C_6-C_{12})$-arylmercapto, $(C_6-C_{12})$-arylsulfinyl, $(C_6-C_{12})$-arylsulfonyl, $(C_7-C_{12})$-aralkylmercapto, $(C_7-C_{12})$-aralkylsulfinyl, $(C_7-C_{12})$-aralkylsulfonyl, $(C_6-C_{12})$-aryloxy, $(C_7-C_{16})$-aralkyloxy, carboxyl, $(C_1-C_{20})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{20})$-alkenyloxycarbonyl, retinyloxycarbonyl, $(C_2-C_{20})$-alkynyloxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_3-C_8)$-cycloalkoxy-$(C_1-C_6)$-alkoxycarbonyl, $(C_6-C_{12})$-aryloxy-$(C_1-C_6)$-alkoxycarbonyl, $(C_7-C_{16})$-aralkoxy-$(C_1-C_6)$-alkoxycarbonyl, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N,N-dicyclo-$(C_3-C_8)$-alkylcarbamoyl, N-$(C_1-C_{10})$-alkyl-N-$(C_3-C_8)$-cycloalkylcarbamoyl, N-(($C_3-C_8$)-cycloalkyl-($C_1-C_6$)-alkyl)carbamoyl, N-$(C_1-C_6)$-alkyl-N-(($C_3-C_8$)-cycloalkyl-($C_1-C_6$)-alkyl)carbamoyl, N-(+-dehydroabietylcarbamoyl, N-$(C_1-C_6)$-alkyl-N-(+)-dehydroabietylcarbamoyl, N-$(C_6-C_{12})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-(($C_1-C_{12}$)-alkoxy-($C_1-C_{10}$)alkyl)carbamoyl, N-(($C_6-C_{16}$)-aryloxy-($C_1-C_{10}$)alkyl)carbamoyl, N-(($C_7-C_{16}$)-aralkyloxy-($C_1-C_{10}$)alkyl)carbamoyl, N-$(C_1-C_{10})$-alkyl-N-(($C_1-C_{10}$)-alkoxy-($C_1-C_{10}$)alkyl)carbamoyl, N-$(C_1-C_{10})$-alkyl-N-(($C_6-C_{12}$)-aryloxy-($C_1-C_{10}$)alkyl)carbamoyl, N-$(C_1-C_{10})$-alkyl-N-(($C_7-C_{16}$)-aralkyloxy-($C_1-C_{10}$)alkyl)carbamoyl or $CON(CH_2)_h$ in which a $CH_2$ group can be replaced by O, S, N-$(C_1-C_8)$-alkylimino, N-$(C_3-C_8)$-cycloalkylimino, N-$(C_3-C_8)$-cycloalkyl-$(C_1-C_4)$alkylimino, N-$(C_6-C_{12})$-arylimino, N-$(C_7-C_{16})$-aralkylimino or N-$(C_1-C_4)$-alkoxy-$(C_1-C_6)$-alkylimino, and h is from 3 to 7, where aryl is substituted in the manner defined for $R^1$ and $R^3$, $R^1$ and $R^3$ are identical or different and are hydrogen, halogen, $(C_1-C_{12})$-alkyl, $(C_1-C_{12})$-alkoxy, —O—$[CH_2]_x$—$C_fH_{(2f+1-g)}Hal_g$, $(C_1-C_{12})$-alkoxy-$(C_1-C_{12})$-alkyl, $(C_1-C_8)$-alkoxy-$(C_1-C_{12})$-alkoxy, $(C_1-C_{12})$-alkoxy-$(C_1-C_8)$-alkoxy-$(C_2-C_6)$-alkyl, $(C_7-C_{11})$-aralkyloxy, $(C_3-C_8)$-cycloalkyl, $(C_3-C_8)$-cycloalkyl-$(C_1-C_8)$-alkyl, $(C_3-C_8)$-cycloalkyloxy, $(C_3-C_8)$-cycloalkyl-$(C_1-C_8)$-alkoxy, $(C_3-C_8)$-cycloalkyloxy-$(C_1-C_8)$-alkyl, $(C_3-C_8)$-cycloalkyloxy-$(C_1-C_8)$-alkoxy, $(C_3-C_8)$-cycloalkyl-$(C_1-C_6)$-alkyl-$(C_1-C_6)$-alkoxy, $(C_3-C_8)$-cycloalkyl-$(C_1-C_6)$-alkoxy-$(C_1-C_6)$-alkyl, $(C_3-C_8)$-cycloalkoxy-$(C_1-C_6)$-alkoxy-$(C_1-C_6)$-alkyl, $NR^YR^Z$, $(C_1-C_8)$-alkylmercapto, $(C_1-C_8)$-alkylsulfinyl or $(C_1-C_8)$-alkylsulfonyl, $(C_6-C_{12})$-arylmercapto, $(C_6-C_{12})$-arylsulfinyl, $(C_6-C_{12})$-arylsulfonyl, $(C_7-C_{12})$-aralkylmercapto, $(C_7-C_{11})$- aralkylsulfinyl, $(C_7-C_{11})$-aralkylsulfonyl, substituted $(C_6-C_{12})$-aryloxy-$(C_1-C_6)$-alkyl, $(C_7-C_{11})$-aralkoxy-$(C_1-C_6)$-alkyl, $(C_6-C_{12})$-aryloxy-$(C_1-C_6)$-alkoxy-$(C_1-C_6)$-alkyl, $(C_7-C_{11})$-aralkyloxy-$(C_1-C_6)$-alkoxy-$(C_1-C_6)$-alkyl, $(C_6-C_{12})$-aryloxy, $(C_7-C_{11})$-aralkyloxy, $(C_6-C_{12})$-aryloxy-$(C_1-C_6)$-alkoxy or $(C_7-C_{11})$-aralkoxy-$(C_1-C_6)$-alkoxy, where an aromatic radical carries by 1, 2, 3, 4 or 5 identical or different substituents from the group hydrogen, halogen, cyano, nitro, trifluoromethyl, $(C_1-C_{16})$-alkyl, $(C_1-C_{16})$-alkenyl, $(C_1-C_6)$-hydroxyalkyl, $(C_1-C_{16})$-alkoxy, $(C_1-C_{16})$-alkenyloxy, —O—$[CH_2]_x$—$C_fH_{(2f+1-g)}F_g$, —OCF$_2$Cl, —O—CF$_2$—CHFCl, $(C_1-C_6)$-alkylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, N-$(C_1-C_4)$-alkylcarbamoyl, N,N-di-$(C_1-C_4)$-alkylcarbamoyl, $(C_1-C_6)$-alkylcarbonyloxy, $(C_3-C_8)$-cycloalkylcarbamoyl, phenyl, benzyl, phenoxy, benzyloxy, NR$^Y$R$^Z$, phenylmercapto, phenylsulfonyl, phenylsulfinyl, sulfamoyl, N-$(C_1-C_4)$-alkylsulfamoyl or N,N-di-$(C_1-C_4)$-alkylsulfamoyl, or optionally carries up to 3 of the abovementioned identical or different substituents, and two adjacent carbon atoms of the aralkyloxy radical together carry a chain —[CH$_2$—] and/or —CH=CH—CH=CH—, where a CH$_2$ group of the chain is optionally replaced by O, S, SO, SO$_2$ or NR', R$^1$ and R$^2$ or R$^2$ and R$^3$ form a chain [CH$_2$]$_o$, where o is 3, 4 or 5, or form, together with the pyridine carrying them, a quinoline ring, where R$^{13}$, R$^{14}$, R$^{15}$ and R$^{16}$ are hydrogen, $(C_1-C_{12})$-alkyl, $(C_1-C_{12})$-alkenyl, chlorine, fluorine, bromine, trifluoromethyl, $(C_1-C_{12})$-alkylsulfonyl, $(C_1-C_{12})$-alkylsulfinyl, phenylsulfonyl, phenylsulfinyl; where phenyl is optionally substituted by fluorine, chlorine or $(C_1-C_5)$-alkoxy, $(C_1-C_{10})$-alkoxy, —O—$[CH_2]_x$—$C_fH_{(2f+1-g)}$, F$_g$ or a radical of the formula D

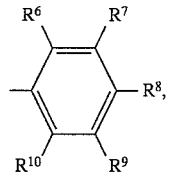

OZ             (D), where Z is [CH$_2$]$_v$—[O]$_w$—[CH$_2$]$_t$—E, in which E is a substituted phenyl radical of the formula F or a substituted heteroaryl radical or a substituted $(C_3-C_8)$-cycloalkyl radical, where v is 0, 1, 2, 3, 4, 5 or 6, w is 0 or 1, and t is 0, 1, 2 or 3, with the restriction that v is not 0 if w is 1, and R$^6$, R$^7$, R$^8$, R$^9$ and R$^{10}$ are identical or different and are hydrogen, halogen, cyano, nitro, trifluoromethyl, $(C_1-C_6)$-alkyl, $(C_3-C_8)$-cycloalkyl, $(C_1-C_6)$-alkoxy, —O—$[CH_2]_x(C_fH_{(2f+1-g)}F_g$, —OCF$_2$Cl, —O—CF$_2$—CHFCl, $(C_1-C_6)$-alkylmercapto, $(C_1-C_6)$-hydroxyalkyl, $(C_1-C_6)$-alkoxy-$(C_1-C_6)$-alkoxy, $(C_1-C_6)$-alkoxy-$(C_1-C_6)$-alkyl, $(C_1-C_6)$-alkylsulfinyl, $(C_1-C_6)$-alkylsulfonyl, $(C_1-C_6)$-alkylcarbonyl, $(C_1-C_8)$-alkoxycarbonyl, carbamoyl, N-$(C_1-C_8)$-alkylcarbamoyl, N,N-di-$(C_1-C_8)$-alkylcarbamoyl, $(C_7-C_{11})$-aralkylcarbamoyl which is optionally substituted by fluorine, chlorine, bromine, trifluoromethyl or $(C_1-C_6)$-alkoxy, N-$(C_3-C_8)$-cycloalkylcarbamoyl, N-$(C_3-C_8)$-cycloalkyl-$(C_1-C_4)$-alkylcarbamoyl, $(C_1-C_6)$-alkylcarbonyloxy, phenyl, benzyl, phenoxy, benzyloxy, NR'R", such as amino, anilino, N-methylanilino, phenylmercapto, phenylsulfonyl, phenylsulfinyl, sulfamoyl, N-$(C_1-C_8)$-alkylsulfamoyl or N,N-di-$(C_1-C_8)$-alkylsulfamoyl, or two adjacent substituents together are a chain —[CH$_2$]$_n$ or —CH=CH—CH=CH—, where a CH$_2$ group of the chain is optionally replaced by O, S, SO, SO$_2$ or NR', if R$^1$ and/or R$^3$ have the meaning of $(C_6-C_{12})$-aryloxy, $(C_7-C_{11})$-aralkyloxy, $(C_6-C_{12})$-aryloxy-$(C_1-C_6)$-alkoxy, $(C_7-C_{11})$-aralkoxy-$(C_1-C_6)$-alkoxy or a corresponding radical containing terminal cycloalkyl groups, this radical is then preferably a radical of the formula D

OZ             (D), where Z is [CH$_2$]$_v$—[O]$_w$—[CH$_2$]$_t$—E, if R$^1$ and/or R$^3$ have the meaning of $(C_7-C_{11})$-aralkyl, $(C_6-C_{12})$-aryloxy-$(C_1-C_6)$-alkyl, $(C_7-C_{11})$-aralkoxy-$(C_1-C_6)$-alkyl or a corresponding radical containing terminal cycloalkyl groups, this radical is then preferably a radical of the formula Z, where Z has the above meaning, but v is not 0, and R$^4$ is hydrogen, R$^Y$ and R$^Z$ are identical or different and are hydrogen, $(C_6-C_{12})$-aryl, $(C_1-C_{10})$-alkyl, $(C_3-C_{10})$-cycloalkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkanoyl, optionally substituted $(C_7-C_{16})$-aralkanoyl or optionally substituted $(C_6-C_{12})$-aroyl, or R$^Y$ and R$^Z$ together are —[CH$_2$]$_{h-}$ in which a CH$_2$ group can be replaced by O, S, N-$(C_1-C_4)$-alkanoylimino or N-$(C_1-C_4)$-alkoxycarbonylimino, and f is 1 to 8, g is 0 or 1 to (2f+1), h is 3 to 6, x is 0 to 3, and n is 3 or 4, including the physiologically active salts.

Compounds of the formula I are particularly preferred in which

Q is O or S,

X is O,

Y is CR$^3$, m is 0,

A is a $(C_1-C_2)$-alkylene group,

B is CO$_2$H,

R$^2$ is hydrogen, bromine, chlorine, cyano, $(C_1-C_{18})$-alkyl, $(C_1-C_8)$-alkoxy, $(C_1-C_{18})$-alkoxymethyl, $(C_2-C_{18})$-alkenyloxymethyl, $(C_2-C_{18})$-alkynyloxymethyl, carbamoyl, N-$(C_1-C_{10})$-alkylcarbamoyl, N-$((C_1-C_{12})$-alkoxy-$(C_1-C_4)$-alkyl)carbamoyl, N,N-di-$(C_1-C_8)$-alkylcarbamoyl, N-$(C_3-C_8)$-cycloalkylcarbamoyl, N-$(C_6-C_{12})$-phenylcarbamoyl, N-$(C_7-C_{12})$-phenylalkylcarbamoyl, N-$(C_1-C_6)$-alkyl-N-$(C_6-C_{12})$phenylcarbamoyl, N-$(C_1-C_6)$-alkyl-N-$(C_7-C_{12})$-phenylalkylcarbamoyl, N-$((C_1-C_6)$-alkoxy-$(C_1-C_6)$alkyl)carbamoyl, carboxyl, $(C_1-C_{20})$-alkoxycarbonyl, $(C_2-C_{20})$-alkenyloxycarbonyl, retinyloxycarbonyl, $(C_3-C_8)$-cycloalkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, phenyl- ($C_1$–$C_6$)-alkoxycarbonyl, phenoxy-($C_1$–$C_6$)-alkoxycarbonyl or benzyloxy-($C_1$–$C_6$)-alkoxycarbonyl, where a phenyl radical is substituted in the manner defined for $R^1$ and $R^3$, and one of the radicals $R^1$ or $R^3$ is hydrogen and the other a radical from the group hydrogen, fluorine, chlorine, ($C_1$–$C_8$)-alkyl, ($C_1$–$C_{10}$)-alkoxy, ($C_5$–$C_6$)-cycloalkyl, ($C_5$–$C_6$)-cycloalkyl-($C_1$–$C_6$)-alkyl, ($C_5$–$C_6$)-cycloalkyloxy, ($C_5$–$C_6$)-cycloalkyl-($C_1$–$C_6$)-alkoxy, ($C_5$–$C_6$)-cycloalkyloxy-($C_1$–$C_6$)-alkyl, ($C_5$–$C_6$)-cycloalkyloxy-($C_1$–$C_6$)-alkoxy, ($C_5$–$C_6$)-cycloalkyl-($C_1$–$C_4$)-alkyl-($C_1$–$C_4$)-alkoxy, ($C_5$–$C_6$)-cycloalkyl-($C_1$–$C_4$)-alkoxy-($C_1$–$C_2$)-alkyl, ($C_5$–$C_6$)-cycloalkoxy-($C_1$–$C_4$)-alkoxy-($C_1$–$C_2$)-alkyl, —O—[$CH_2$]$_x$—$C_fH_{(2f+1-g)}F_g$, ($C_1$–$C_6$)-alkoxy-($C_1$–$C_6$)-alkyl, ($C_1$–$C_6$)-alkoxy-($C_1$–$C_6$)-alkoxy, ($C_1$–$C_6$)-alkoxy-($C_1$–$C_4$)-alkoxy-($C_1$–$C_2$)-alkyl, substituted ($C_6$–$C_{12}$)-phenoxy, ($C_7$–$C_{11}$)-phenylalkyloxy, ($C_6$–$C_{12}$)-phenoxy-($C_1$–$C_6$)-alkoxy or ($C_7$–$C_{11}$)-phenylalkoxy-($C_1$–$C_6$)-alkoxy, phenoxy-($C_1$–$C_4$)-alkyl, ($C_7$–$C_{11}$)-phenylalkyloxy-($C_1$–$C_4$)-alkyl, phenoxy-($C_1$–$C_4$)-alkoxy-($C_1$–$C_2$)-alkyl or ($C_7$–$C_{11}$)-phenylalkyloxy-($C_1$–$C_4$)-alkoxy-($C_1$–$C_2$)-alkyl, where an aromatic radical is substituted by 1, 2 or 3 identical or different substituents from the group fluorine, chlorine, cyano, trifluoromethyl, ($C_1$–$C_{12}$)-alkyl, ($C_2$–$C_{12}$)-alkenyl, ($C_2$–$C_{12}$)-alkenyloxy or ($C_1$–$C_{12}$)-alkoxy, and $R^4$ is hydrogen and if $R^1$ or $R^3$ has the meaning of ($C_6$–$C_{12}$)-phenoxy, ($C_7$–$C_{11}$)-phenylalkyloxy, ($C_6$–$C_{12}$)-phenoxy-($C_1$–$C_6$)-alkoxy, ($C_7$–$C_{11}$)-phenylalkoxy-($C_1$–$C_6$)-alkoxy, ($C_5$–$C_6$)-cycloalkyloxy, ($C_5$–$C_6$)-cycloalkyl-($C_1$–$C_6$)-alkoxy, ($C_5$–$C_6$)-cycloalkoxy-($C_1$–$C_6$)-alkoxy or ($C_5$–$C_6$)-cycloalkyl-($C_1$–$C_4$)-alkyl-($C_1$–$C_4$)-alkoxy, this radical is then, especially, a radical of the formula D $$OZ \qquad (D),$$

in which Z is —[$CH_2$]$_v$—[O]$_w$—[$CH_2$]$_t$—E,
where E is a substituted phenyl radical of the formula F

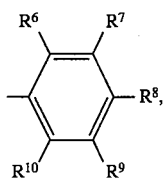

or a ($C_3$–$C_8$)-cycloalkyl radical, where v is 0, 1, 2 or 3, w is 0 or 1, and t can be 0 or 1, with the restriction that v is not 0 if w is 1, and in which $R^6$, $R^7$, $R^8$, $R^9$ and $R^{10}$ are identical or different and are hydrogen, fluorine, chlorine, cyano, trifluoromethyl, ($C_1$–$C_6$)-alkyl, ($C_1$–$C_6$)-alkoxy, —O—[$CH_2$]$_x$—($C_fH_{(2f+1-g)}F_g$, N-($C_1$–$C_8$)-alkylcarbamoyl, N,N-di-($C_1$–$C_8$)-alkylcarbamoyl, N-($C_3$–$C_8$)-cycloalkylcarbamoyl or ($C_7$–$C_{11}$)-phenylalkylcarbamoyl which is optionally substituted by fluorine, chlorine, trifluoromethyl or ($C_1$–$C_6$)-alkoxy, or if $R^1$ or $R^3$ has the meaning of phenyl, phenoxy-($C_1$–$C_6$)-alkyl, ($C_7$–$C_{11}$)-phenylalkyl, ($C_7$–$C_{11}$)-phenylalkyloxy-($C_1$–$C_4$)-alkyl, ($C_5$–$C_6$)-cycloalkyl, ($C_5$–$C_6$)-cycloalkyl-($C_1$–$C_6$)-alkyl, ($C_5$–$C_6$)-cycloalkoxy-($C_1$–$C_4$)-alkyl, ($C_5$–$C_6$)-cycloalkyl-($C_1$–$C_4$)-alkoxy-($C_1$–$C_2$)-alkyl or ($C_5$–$C_6$)-cycloalkoxy-($C_1$–$C_4$)-alkoxy-($C_1$–$C_2$)-alkyl, this radical is then, especially, a radical of the formula Z, in which v is 1, 2, 3 or 4, w is 0, and t is 0, or
v is 1, 2, 3 or 4, w is 1, and t is 0, or
v is 1, 2, 3 or 4, w is 1, and t is 1.

Compounds of the formula I are very particularly preferred in which

Q is O or S, preferably O,

X is O,

Y is $CR^3$, m is 0,

A is a —$CH_2$— group,

B is —$CO_2H$, $R^1$ is hydrogen, $R^2$ and $R^3$, together with the pyridine carrying them, form a quinoline ring, where $R^{13}$, $R^{15}$ and $R^{16}$ are hydrogen, $R^{14}$ is hydrogen, ($C_1$–$C_{12}$)-alkyl, ($C_1$–$C_{12}$)-alkenyl, chlorine, fluorine, bromine, trifluoromethyl, ($C_1$–$C_{12}$)-alkylsulfonyl, ($C_1$–$C_{12}$)-alkylsulfinyl, phenylsulfonyl, phenylsulfinyl; where phenyl is optionally substituted once by fluorine, chlorine or ($C_1$–$C_5$)-alkoxy, ($C_1$–$C_{10}$)-alkoxy, —O—[$CH_2$]$_x$—$C_fH_{(2f+1-g)}$, $F_g$, or benzyloxy, optionally substituted once in the phenyl ring by fluorine, chlorine or ($C_1$–$C_5$)-alkoxy, and $R^4$ is hydrogen, including the physiologically active salts.

Compounds of the formula I are preferred in the highest degree in which

Q is O,

X is O,

Y is $CR^3$, m is 0,

A is a —$CH_2$— group,

B is $CO_2H$, $R^1$ is hydrogen, ($C_1$–$C_{10}$)-alkoxy, ($C_5$–$C_6$)-cycloalkyloxy, ($C_5$–$C_6$)-cycloalkyl-($C_1$–$C_2$)-alkoxy, —O—[$CH_2$]$_x$—$C_fH_{(2f+1-g)}F_g$, ($C_1$–$C_4$)-alkoxy-($C_1$–$C_4$)-alkoxy, substituted phenoxy or substituted benzyloxy, where the phenyl radical is substituted by a substituent from the group fluorine, chlorine, cyano, trifluoromethyl, ($C_1$–$C_4$)-alkyl or ($C_1$–$C_4$)-alkoxy, and $R^2$, $R^3$ and $R^4$ are hydrogen, including the physiologically active salts.

The compounds of the formula I are furthermore preferred in the highest degree in which Q is S, X is O, Y is $CR^3$, m is 0, A is a —$CH_2$— group, B is —$CO_2H$, $R^1$ is hydrogen, and $R^2$, $R^3$ and $R^4$ are hydrogen.

The compounds of the formula I are furthermore preferred in the highest degree in which Q is O, X is O, Y is $CR^3$, m is 0, A is a —$CH_2$— group, B is —$CO_2H$, $R^1$ is hydrogen, and $R^2$ and $R^3$, together with the pyridine carrying them, form a quinoline ring, and $R^4$ is hydrogen.

The invention also embraces prodrugs for the compounds of the formula (I), which prodrugs bring about an inhibition of collagen biosynthesis in vivo by liberating compounds of the formula I or their salts.

Finally, the invention also embraces prodrugs which, by liberating compounds of the formula I or their salts, bring about an inhibitory effect in vivo on prolyl-4-hydroxylase.

Prodrug groupings are chemical groups which, in vivo, are converted into the carboxylate group of the compounds of the formula I, and/or can be cleaved from the amide N atom, and/or can be converted into a pyridine ring.

Those prodrug groups which are suitable are known to the person skilled in the art.

The following prodrug groupings receive particular mention:

for the carboxylate group, ester groups, amide groups, hydroxymethyl groups and aldehyde groups, and their derivatives; for the pyridine N atom, N-oxides and N-alkyl derivatives; and for the pyridine ring, 1,4-dihydro- and tetrahydropyridine derivatives.

The invention relates to the use of compounds of the formula I, and also the physiologically tolerated salts, for inhibiting collagen biosynthesis.

The invention relates to the use of compounds of the formula I, and also the physiologically tolerated salts, for inhibiting prolyl-4-hydroxylase.

The invention also relates to the use of compounds of the formula I, and also the physiologically tolerated salts, for producing a pharmaceutical against fibrotic diseases.

The invention also relates to the use of compounds of the formula I, and also the physiologically tolerated salts, for producing a pharmaceutical against fibrotic diseases of the liver, the lung and the skin.

Finally, the invention relates to compounds of the formula I for use as pharmaceuticals.

The invention relates, in particular, to the compounds of the formula I for use as fibrosuppressive agents.

The invention also relates to a process for preparing compounds of the formula I.

The compounds of the formulae I and I', in which

X is O

A—B is —$(CH_2)_{1-4}$—$CO_2H$ and m is 0 and 1, are prepared by i1.) reacting pyridine-2-carboxylic acids of the formula II ($R^{11}$ is H) with the amino esters of the formula III to form the amide esters of the formula IV, or i2.) reacting pyridine-2-carboxylic esters of the formula II ($R^{11}$ is lower alkyl), under the conditions of aminolysis, to form the compounds of the formula IV;

ii) liberating the compounds of the formulae I and V from their esters of the formula IV; and iii) oxidizing the compounds of the formulae IV, V or I with an oxidizing agent to form the pyridine N-oxides of the formulae I' and VI and, where appropriate, subsequently hydrolyzing the compounds IV to form the pyridine N-oxides of the formula I'.

The reactions i1); i2) and ii) can be carried out using compounds in which $R^{11}$ is H or using compounds in which $R^{11}$ is an O-protective group.

Examples of suitable protective groups, as are familiar to the person skilled in the art, are methyl, ethyl, MEM, MOM, benzyl, 4-MeO-benzyl or 3,4-dimethoxybenzyl.

Additional protective groups, and the conditions for their elimination (conversion of compounds of the formula V into compounds of the formula I), are described by Theodoro W. Greene and Peter G. M. Wuts, in Protective Groups in Organic Synthesis, Second Edition 1981, John Wiley, Chapters 2 and 3.

Scheme 1

A—B is $(CH_2)_{1-4}$—$CO_2H$

Q is O or S $R^{10}$ is $R^4$ or PG (protecting group)

$R^{11}$ is H, $(C_1-C_8)$-alkyl or benzyl $R^{12}$ is H, $(C_1-C_8)$-alkyl or benzyl The methods of carboxyl activation and the condensation reactions known from peptide chemistry are suitable processes for the amide formation (reaction i1)).

The substances which are known to the person skilled in the art, such as thionyl chloride, oxalyl chloride, pivaloyl chloride, chloroformate derivatives, and N,N'-carbonyldiimidazole, can be used as reagents for the carboxylic acid activation. The activated derivatives of the compounds of the formula II are prepared in situ and then reacted with the amide derivatives of the formula III.

An example of a suitable condensing agent is the combination of N,N'-dicyclohexylcarbodiimide, 1-hydroxy-1H-benzotriazole and N-ethylmorpholine.

Suitable solvents are dichloromethane, tetrachloromethane, butyl acetate, ethyl acetate, toluene, tetrahydrofuran, dimethoxyethane, 1,4-dioxane, acetonitrile, N,N-dimethylformamide, N,N-dimethylacetamide, dimethyl sulfoxide, nitromethane and/or pyridine.

3-Hydroxypyridine-2-carboxylic acid can be acquired commercially. 3-Mercaptopyridine-2-carboxylic acid is disclosed in Roczniki Chemji 1932, 493.

The 2-hydroxymethylpyridines of the formula VIIa, which are disclosed in EP-A-0 304 732, EP-A-0 321 385 and EP-A-0 208 452, can be used as intermediates for preparing derivatives which are substituted in the 4 position ($R^1$) (Q is O).

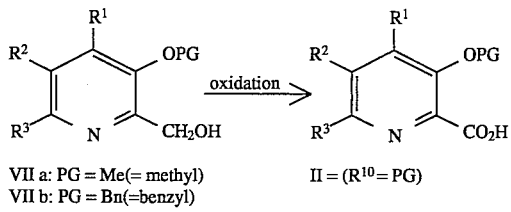

VII a: PG = Me(= methyl)     II = ($R^{10}$ = PG)
VII b: PG = Bn(=benzyl)

The 3-O-benzyl derivatives of the formula VIIb are also obtained in an analogous manner, as described in those documents.

The compounds of the formulae VIIa and VIIb were reacted with an oxidizing agent, preferably with $KMnO_4$, in aqueous alkaline medium, to form the pyridine-2-carboxylic acid derivatives of the formula II ($R^{10}$ is PG).

The compounds of the formula I are inhibitors of prolyl-4-hydroxylase. The inhibition of this enzyme was determined, as described by Kaule and Günzler in anal. Biochem. 184, 291 to 297 (1990).

The novel compounds of the formula I furthermore possess valuable pharmacological properties and exhibit, in particular, antifibrotic activity.

The antifibrotic effect can be determined using the model of carbon tetrachloride-induced hepatic fibrosis. For this, rats are treated twice a week with $CCl_4$ (1 ml/kg)—dissolved in olive oil. The substance under test is administered daily, where appropriate even twice a day, per os, or intraperitoneally—dissolved in a suitable tolerated solvent. The extent of the hepatic fibrosis is determined by histology, and the proportion of collagen in the liver is analyzed by means of determining hydroxyproline—as described in Kivirikko et al. (Anal. Biochem. 19, 249 f. (1967)). The fibrogenic activity can be measured by the radioimmunological determination of collagen fragments and procollagen peptides in the serum. In this model, the novel compounds are active at a concentration of from 1 to 100 mg/kg.

The fibrogenic activity can be measured by radioimmunological determination of the N-terminal propeptide of collagen type III or of the N-terminal or C-terminal crosslinking domain of collagen type IV (7s collagen or type IV collagen $NC_1$) in the serum.

For this purpose, measurements were made of the concentrations of hydroxyproline, procollagen III peptide, 7s collagen and type IV collagen NC in the liver of a) untreated rats (control)

b) rats which were administered carbon tetrachloride ($CCl_4$ control)

c) rats which were first administered $CCl_4$ and then a novel compound (this test method is described by Rouiller, C., Experimental toxic injury of the liver; in The Liver, C. Rouiller, vol. 2, 5. 335 to 476, New York, Academic Press, 1964).

Activity of the compounds according to the invention can furthermore be demonstrated in the following systems.

Inhibition of hepatic prolyl-4-hydroxylase in vivo:

This model is used to detect acute inhibition of prolyl-4-hydroxylase in vivo. For this, rats of either sex (healthy or with induced hepatic fibrosis) are administered (intraperitoneally, intravenously or per os) the test substance or the corresponding vehicle and then $^{14}$C-L-Prolin, which is administered intraperitoneally (250 µCi/kg of body weight). After that, there is a second intraperitoneal administration of $^{14}$C-L-Prolin (250 µCi/kg of body weight). Finally, the animals are exsanguinated under pentobarbital anaesthesia and the livers removed. The hepatic collagen was purified, in accordance with published protocols (ref. 1, and 2) by pepsin digestion and fractional ammonium sulfate precipitation. The purified liver collagen was hydrolyzed and the content of $^{14}$C-hydroxyprolin and $^{12}$C-prolin was determined by amino acid analysis using ion exchange chromatography. Inhibition of the prolyl-4-hydroxylase is indicated by a decrease in the quotient $^{14}$C-hydroxyprolin/[$^{14}$C-hydroxyprolin+$^{14}$C-prolin]. 2,2'-Dipyridyl is used as the reference substance. (Ref. 1: Chojkier, M. 1986. Hepatocyte collagen production in vivo in normal rats. J. Clin. Invest. 78: 333–339 and Ref. 2: Ogata I., et al. 1991. Minor contribution of hepatocytes to collagen production in normal and early fibrotic livers. Hepatology 14: 361–367).

Inhibition of prolyl-4-hydroxylase in cell cultures:

The following cell types are used for testing inhibitors of prolyl-4-hydroxylase in cell cultures: Normal human fibroblasts (NHDF), rat liver epithelial cells (Ref. 1) and primary fat storing cells (Ref. 2) from rat liver. For this, the cells are cultivated in the presence of inhibitors. At the same time, the collagen which is newly synthesized during this period is metabolically labelled with 4-$^3$H-L-prolin and $^{14}$C-prolin. The effect of the test substances on the degree of hydroxylation of the collagen is then determined by the method of Chojkier et al. (Ref. 3). 2,2'-Dipyridyl is employed as the reference substance. (1.: Schrode, W., Mecke, D., Gebhard, R. 1990. Induction of glutamine synthetase in periportal hepatocytes by co-cultivation with a liver epithelial cell line. Eur. J. Cell. Biol. 53: 35–41, 2. Blomhoff, R., Berg T. 1990. Isolation and cultivation of rat liver stellate cells. Methods Enzymol. 190: 59–71 and 3.: Chojkier, M. Peterkofsky, B. Bateman, J. 1980. A new method for determining the extent of proline hydroxylation by measuring changes in the ration of [4-$^3$H]:[$^{14}$C]proline in collagenase digests. Anal. Biochem. 108: 385–393).

The compounds of the formula I may be used as medicaments in the form of pharmaceutical preparations, which contain the compounds, where appropriate together with tolerated pharmaceutical excipients. The compounds can be used as medicines, for example in the form of pharmaceutical preparations which contain these compounds in a mixture together with a pharmaceutical, organic or inorganic excipient which is suitable for enteral, percutaneous or parenteral administration, such as, for example, water, gum arabic, gelatin, lactose, starch, magnesium stearate, talc, vegetable oils, polyalkylene glycols, vaseline, etc.

For this purpose, they can be administered orally in doses of from 0.1 to 25 mg/kg/day, preferably of from 1 to 5 mg/kg/day, or parenterally in doses of from 0.01 to 5 mg/kg/day, preferably of from 0.01 to 2.5 mg/kg/day, in particular of from 0.5 to 1.0 mg/kg/day. The dosage can also be increased in severe cases. In many cases, however, smaller doses are also sufficient. These data refer to an adult of about 75 kg in weight.

In the examples described below, the compounds of the formula I according to the invention are designated substituted heterocyclic carboxylic acid glycylamides, preferably pyridine-2-carboxylic acid glycylamides. This designation is understood to mean substituted pyridine-2-carboxylic acid N-(carboxymethyl)amides. A further option is to classify the compounds as substituted N-(pyridyl-2-carbonyl)glycines.

EXAMPLE 1

3-Hydroxypyridine-2-carboxylic acid glycylamide a) 3-Benzyloxypyridine-1-carboxylic acid 2.78 g (20 mmol) of 3-hydroxypyridine-2-carboxylic acid were added, at 25° C., to 1.76 g (44 mmol) of sodium hydride (60% in mineral oil) in 35 ml of anhydrous N,N-dimethylformamide. the mixture was stirred at 25° C. for 1 hour and 5.06 ml (44 mmol) of benzyl chloride were then added and the mixture was heated to boiling for 2 hours; it was then cooled to 25° C. and concentrated in vacuo, with the residue being taken up in diethyl ether; this latter mixture was extracted twice with water, with a saturated aqueous solution of sodium bicarbonate and with a saturated solution of sodium chloride. Once the organic phase had been dried and concentrated in vacuo, the brown crude product was chromatographed on silica gel using n-heptane/ethyl acetate (1:1). The 2.46 g (17 mmol) of the benzyl ester thus obtained were hydrolyzed in tetrahydrofuran/methanol (2:1) using 17 ml (17 mmol) of a 1N solution of sodium hydroxide. After 48 hours at 25° C., citric acid was added and the mixture was concentrated in vacuo and the residue chromatographed on silica gel using ethyl acetate/methanol (1:1). 1.38 g of product were obtained in the form of pale yellow crystals, m.p. 64°–66° C.

b) 2-Benzyloxypyridine-2-carboxylic acid (glycyl methyl ester)amide 1.38 g (6 mmol) of the above carboxylic acid were stirred in 30 ml of anhydrous tetrahydrofuran, at 0° C. for 30 minutes, together with 1.7 ml (12.1 mmol) of triethylamine. 0.81 ml (66 mmol) of pivaloyl chloride was then added and the mixture was stirred at 0° C. for 3 hours; 0.92 g (6.6 mmol) of glycine methyl ester hydrochloride and 0.85 ml (6 mmol) of triethylamine were added and the mixture was then stirred at 0° C. for 1 hour, warmed to 20° C. and concentrated in vacuo; the residue was taken up in 100 ml of ethyl acetate and this mixture was extracted with a saturated aqueous solution of sodium bicarbonate and a saturated solution of NaCl and, after drying, concentrated in vacuo; the residue was purified by flash chromatography on silica gel using ethyl acetate/methanol (10:1). 1.02 g were obtained of an oil which was colored pale pink.

c) 3-Hydroxypyridine-2-carboxylic acid (glycyl methyl ester)amide 1.02 g (3.4 mmol) of the above benzyl ester were dissolved in 50 ml of methanol and, after that, 50 mg of Pd/C (10% Pd) were added and the mixture was hydrogenated in a hydrogenation vessel until no further hydrogen uptake took place (uptake, approximately 60 ml of hydrogen). The mixture was filtered through celite and concentrated in vacuo; the residue was purified by flash chromatography on silica gel using ethyl acetate/n-heptane (3:1), and 580 mg of colorless crystalline product were obtained, m.p. 59°–61° C.

d) The title compound was obtained by dissolving 0.45 g (2.1 mmol) of the above methyl ester in 15 ml of tetrahydrofuran/methanol (21:1) and then adding 5 ml of a 1N aqueous solution of sodium hydroxide. The mixture was stirred at 20° C. for 24 hours and concentrated in vacuo; the residue was taken up in water and this mixture was acidified to pH 3–4 with 2N hydrochloric acid. In association with this, the product crystallized in the form of colorless crystals which, after having been filtered off with suction, were freed from remaining water in an IR drying apparatus. 185 mg were obtained of the title compound, m.p. 182°–174° C.

EXAMPLE 2

3-Hydroxypyridine-2-carboxylic acid (β-alanyl)amide a) 3-Hydroxypyridine-2-carboxylic acid (β-alanyl methyl ester)amide 2.78 g (20 mmol) of 3-hydroxypyridine-2-carboxylic acid were suspended in 80 ml of anhydrous tetrahydrofuran and, after that, 2.72 g (20 mmol) of β-alanine methyl ester hydrochloride, 2.55 ml (20 mmol) of N-ethylmorpholine and 5.41 g (40 mmol) of 1-hydroxy-1H-benzotriazole were added and then the mixture was cooled down to 0° C. and 4.33 g (21 mmol) of N,N'-dicyclohexylcarbodiimide in 20 ml of tetrahydrofuran were added. The mixture was then stirred at 0° C. for 70 minutes and then at 20° C. for 60 minutes, with the solid which precipitates out being filtered off and the filtrate concentrated in vacuo; the residue was taken up on 100 ml of dichloromethane and this mixture was washed with water and the organic phase then dried and concentrated, and the residue purified on silica gel using ethyl acetate/methanol (5:1), 1.24 g of colorless oil.

b) The title compound was obtained by hydrolyzing 1.2 g (5.4 mmol) of the above methyl ester, at 20° C. for 5 hours, in 100 ml of ethanol/tetrahydrofuran (1:1) using 10 ml of a 1N aqueous solution of sodium hydroxide. The mixture was concentrated in vacuo and the residue was taken up in water and this solution was extracted three times with 25 ml of dichloromethane on each occasion. The aqueous phase was acidified to pH 2 and the resulting precipitate was filtered off with suction and washed with cold water and with cold diethyl ether. 0.6 g of the title compound were obtained, m.p. 206° C. (decomp.)

EXAMPLE 3

3-Hydroxy-4-methoxypyridine-2-carboxylicacidglycylamide a) 3-Benzyloxy-4-hydroxy-2-methylpyridine 200 g (1.6 mol) of 3-hydroxy-2-methyl-4-pyranone (maltol) were dissolved for 1 hour in 800 ml of a 2N solution of sodium hydroxide (1.6 mol), and after that a solution of 343 g (237 ml, 2.0 mol) of benzyl bromide in 250 ml of tetrahydrofuran was added. Monitoring by TLC indicated that approximately 25% transformation had taken place after 15 minutes. The reaction mixture was then stirred at 60° C. for 2 hours and left to stand at 20° C. for 12 hours; the upper phase was separated off and the lower phase was extracted with diethyl ether and the organic phases were then concentrated together in vacuo. 1 l of concentrated, aqueous ammonia and 500 ml of 1,4-dioxane were added to the evaporation residue which had been obtained and the mixture was warmed on a steam bath. 250 ml volumes of ammonia solution were added at 60 minute intervals on each of 6 occasions. After 8 hours, monitoring by TLC indicated that transformation was complete. Once the mixture had been cooled down, the lower, brown phase was separated off and the product was crystallized by adding ethyl acetate and then filtered off with suction, washed with ethyl acetate and dried. 230 g of product were obtained, m.p. 165°–167° C. A further 45 g of product were successfully obtained from the aqueous mother liquor.

b) 3-Benzyloxy-4-chloro-2-methylpyridine 1-oxide 21 g (0.098 mol) of 3-benzyloxy-4-hydroxy-2-methylpyridine were introduced, at 25° C. and while stirring, into 200 ml of phosphorus oxychloride, and the mixture was heated under reflux for 7 hours. Phosphorus oxychloride was subsequently distilled off in vacuo and the residue was introduced in portions into 1 l of water; the small amount of undissolved material was separated off and the aqueous phase was extracted three times with 200 ml of dichloromethane on each occasion; the organic phase was dried with magnesium sulfate and concentrated and the residue was treated with diethyl ether; 1 g of crystalline product (as the hydrochloride) was filtered off with suction, m.p. 148°–150° C., and 10 g (43 mmol) of oily product were isolated. The latter was dissolved in 100 ml of dichloromethane and, after that, 12.5 g of 3-chloro-perbenzoic acid (50 mmol) were added in portions, at 25° C. and while stirring, and the mixture was then stirred for 1 hour. Ammonia gas was then passed in the precipitated ammonium salts were filtered off with suction and washed with dichloromethane; ammonia gas was passed in a second time and the small amount of crystalline material was filtered off and the filtrate was concentrated in vacuo; the residue was treated with diisopropyl ether. 8.0 g of product were obtained.

c) 3-Benzyloxy-4-methoxy-2-methylpyridine 1-oxide 8 g (32 mmol) of the above compound were introduced in portions, at 25° C. and while stirring, into 200 ml of a methanolic solution of sodium methoxide (from 0.83 g (36 mmol) of Na). After the mixture had been heated under reflux for 2 hours, monitoring by TLC (ethyl acetate/methanol=5:1) indicated that 20% transformation had occurred. 5.7 ml (32 mmol) of a 30% solution of NaOMe in methanol were added and the mixture was heated to boiling for 4 hours; the same quantity of NaOMe solution was added once again and the mixture was heated to boiling for a further 4 hours. After the mixture had been cooled down to 25° C., it was concentrated in vacuo and 100 ml of water were added to the residue; the latter mixture was extracted three times with 100 ml of dichloromethane on each occasion and the organic phase was dried and concentrated and the residue was crystallized using diisopropyl ether. 6.0 g of product were obtained, m.p. 84°–86° C.

d) 3-Benzyloxy-2-hydroxymethyl-4-methoxypyridine 6.0 g (25.5 mmol) of the above N-oxide were dissolved in 20 ml of glacial acetic acid and, after that, 30 ml of acetic anhydride were added dropwise, at 80° C. and while stirring, and the mixture was then heated at 90° C. for 1 hour. Monitoring by TLC (ethyl acetate/methanol=5:1) indicated that 20% transformation had taken place. After a further 30 minutes at 120° C., the reaction was complete. The mixture was cooled to 80° C. and 15 ml of methanol were added; the mixture was next heated to boiling for 15 minutes and then clarified over active charcoal and concentrated in vacuo; the residue, dissolved in a little methanol, was added to 200 ml of 1.5N methanolic NaOH. After 1 hour, the mixture was concentrated in vacuo and the residue was taken up in 200 ml of water; this solution was extracted three times by shaking with 150 ml of ethyl acetate on each occasion and the organic phase was dried over $MgSO_4$ and concentrated. 4.4 g were obtained of oily crude product which was subjected to further reaction.

e) 3-Benzyloxy-4-methoxypyridine-2-carboxylic acid 4.4 g (18 mmol) of the above 2-hydroxymethyl compound and 1.6 g of potassium hydroxide were dissolved in 100 ml of water and, after that, 2.6 g (16.3 mmol) of potassium permanganate were added in 2 portions, while stirring After 15 minutes, 1.95 g of potassium permanganate were added and the mixture was then stirred for 30 minutes at this temperature. Precipitated $MnO_2$ was filtered off with suction from the hot solution and then washed twice with hot water; the filtrate was concentrated in vacuo to 50 ml and then adjusted to pH 1, while being cooled with ice, using concentrated HCl. The crystalline precipitate was filtered off with suction and dried; 4.6 g of product, m.p. 224°–225° C.

f) 3-Benzyloxy-4-methoxypyridine-2-carboxylic acid (glycyl ethyl ester)amide 2.6 g (10 mmol) of the above pyridine-2-carboxylic acid were dissolved in 250 ml of anhydrous dichloromethane and 80 ml of anhydrous tetrahydrofuran and, after that, 1.4 g (10 mmol) of glycine ethyl ester hydrochloride, 2.8 ml (22 mmol) of N-ethylmorpholine, 1.5 g (11 mmol) of 1-hydroxy-1H-benzotriazole and 2.3 g (11 mmol) of N,N'-dicyclohexylcarbodiimide were added, while stirring, and the mixture was then stirred at 20° C. for 20 minutes. Undissolved material was subsequently filtered off and the mixture was concentrated in vacuo. The residue was dissolved in 200 ml of dichloromethane and this solution was stirred together with 200 ml of a saturated aqueous solution of sodium bicarbonate; the organic phase was separated off, dried and concentrated, and the residue was chromatographed on silica gel using ethyl acetate. 2.0 g were obtained of oily product which was immediately subjected to further reaction under g).

g) 3-Hydroxy-4-methoxypyridine-2-carboxylic acid (glycyl ethyl ester)amide 2.0 g (5.8 mmol) of the above benzyl ether were dissolved in 100 ml of tetrahydrofuran/methanol (1:1) and hydrogenated using Pd/C (10%) in a hydrogenation vessel. Once 130 ml of hydrogen had been taken up, the catalyst was filtered off with suction and the filtrate was concentrated in vacuo and the residue was crystallized using diisopropyl ether. 1.2 g of product were obtained, m.p. 97°–99° C.

h) The title compound was obtained by introducing 0.5 g (1.97 mmol) of the above ethyl ester, while stirring, into 100 ml of 1.5N methanolic NaOH and stirring the mixture at 20° C. for 30 minutes. The mixture was then concentrated in vacuo and the residue was dissolved in water with this solution being adjusted to pH 1 using concentrated HCl. Since no crystallization took place, the solution was concentrated once again and the residue was treated twice with anhydrous ethanol and once with diethyl ether; in each case, the residue was filtered off with suction and the organic solvents were distilled off in vacuo and the residue crystallized using diethyl ether. 160 mg of the title compound were obtained, m.p. 270°–271° C.

EXAMPLE 4

3-Hydroxy-4-methoxypyridine-2-carboxylic acid L-alanylamide

EXAMPLE 5

4-Hexyloxy-3-hydroxypyridine-2-carboxylic acid glycylamide

EXAMPLE 6

4-(3-Ethyloxypropyloxy)-3-hydroxy-pyridine-2-carboxylic acid glycylamide

EXAMPLE 7

3-Hydroxy-4-(2,2,2-trifluoroethyloxy)pyridine-2-carboxylic acid glycylamide

EXAMPLE 8
4-Ethyloxy-3-hydroxypyridine-2-carboxylic acid glycylamide

EXAMPLE 9
4-Butyloxy-3-hydroxypyridine-2-carboxylic acid glycylamide

EXAMPLE 10
3-Hydroxy-4-propyloxypyridine-2-carboxylic acid glycylamide

EXAMPLE 11
3-Hydroxy-4-(2-propyloxy)pyridine-2-carboxylic acid glycylamide

EXAMPLE 12
3-Hydroxy-4-(2-methylpropyloxy)pyridine-2-carboxylic acid glycylamide

EXAMPLE 13
3-Hydroxy-4-pentyloxypyridine-2-carboxylic acid glycylamide

EXAMPLE 14
3-Hydroxy-4-(3-methylbutyloxy)pyridine-2-carboxylic acid glycylamide

EXAMPLE 15
4-(2-Ethylbutyloxy)-3-dihydroxypyridine-2-carboxylic acid glycylamide

EXAMPLE 16
4-(2-Cyclohexylethyloxy)-3-hydroxypyridine-2-carboxylic acid glycylamide

EXAMPLE 17
4-(Cyclohexylmethyloxy)-3-hydroxypyridine-2-carboxylic acid glycylamide

EXAMPLE 18
4-Cyclohexyloxy-3-hydroxypyridine-2-carboxylic acid glycylamide

EXAMPLE 19
3-Hydroxy-4-(3-methoxypropyloxy)pyridine-2-carboxylic acid glycylamide

EXAMPLE 20
3-Hydroxy-4-(2-phenoxyethyloxy)pyridine-2-carboxylic acid glycylamide

EXAMPLE 21
4-Benzyloxy-3-hydroxypyridine-2-carboxylic acid glycylamide

EXAMPLE 22
4-(4-Chlorobenzyloxy)-3-hydroxypyridine-2-carboxylic acid glycylamide

EXAMPLE 23
4-(4-Fluorobenzyloxy)-3-hydroxypyridine-2-carboxylic acid glycylamide

EXAMPLE 24
3-Hydroxy-4-(4-trifluoromethylbenzyloxy)pyridine-2-carboxylic acid glycylamide

EXAMPLE 25
3-Hydroxy-4-(3-trifluoromethylbenzyloxy)pyridine-2-carboxylic acid glycylamide

EXAMPLE 26
3-Hydroxy-4-(4-trifluoromethoxybenzyloxy)pyridine-2-carboxylic acid glycylamide

EXAMPLE 27
4-(3,5-bis(Trifluoromethyl)benzyloxy)-3-hydroxypyridine-2-carboxylic acid glycylamide

EXAMPLE 28
4-(3,5-Dichlorobenzyloxy)-3-hydroxypyridine-2-carboxylic acid glycylamide

EXAMPLE 29
3-Hydroxy-4-(2,2,3,3,3-pentafluoropropyloxy)pyridine-2-carboxylic acid glycylamide

EXAMPLE 30
4-(2,2,3,3,4,4,4-Heptafluorobutyloxy)-3-hydroxypyridine-2-carboxylic acid glycylamide

EXAMPLE 31
3-Hydroxy-4-(2,2,3,3-tetrafluoropropyloxy)pyridine-2-carboxylic acid glycylamide

EXAMPLE 32
4-Ethoxy-3-hydroxypyridine-2-carboxylic acid L-alanylamide

EXAMPLE 33
4-Butyloxy-3-hydroxypyridine-2-carboxylic acid L-alanylamide

EXAMPLE 34
3-Hydroxy-4-propyloxypyridine-2-carboxylic acid L-alanylamide

EXAMPLE 35
3-Hydroxy-4-(2-propyloxy)pyridine-2-carboxylic acid L-alanylamide

EXAMPLE 36
3-Hydroxy-4-(2-methylpropyloxy)pyridine-2-carboxylic acid L-alanylamide

EXAMPLE 37
3-Hydroxy-4-pentyloxpyridine-2-carboxylic acid L-alanylamide

EXAMPLE 38

3-Hydroxy-4-(3-methylbutyloxy)pyridine-2-carboxylic acid L-alanylamide

EXAMPLE 39

4-(2-Ethylbutyloxy)-3-hydroxypyridine-2-carboxylic acid L-alanylamide

EXAMPLE 40

4-(2-Cyclohexylethyloxy)-3-hydroxypyridine-2-carboxylic acid L-alanylamide

EXAMPLE 41

4-(Cyclohexylmethyloxy)-3-hydroxypyridine-2-carboxylic acid L-alanylamide

EXAMPLE 42

4-Cyclohexyloxy-3-hydroxypyridine-2-carboxylic acid L-alanylamide

EXAMPLE 43

3-Hydroxy-4-(3-methoxypropyloxy)pyridine-2-carboxylic acid L-alanylamide

EXAMPLE 44

3-Hydroxy-4-(2-phenoxyethyloxy)pyridine-2-carboxylic acid L-alanylamide

EXAMPLE 45

4-Benzyloxy-3-hydroxypyridine-2-carboxylic acid L-alanylamide

EXAMPLE 46

4-(4-Chlorobenzyloxy)-3-hydroxypyridine-2-carboxylic acid L-alanylamide

EXAMPLE 47

4-(4-Fluorobenzyloxy)-3-hydroxypyridine-2-carboxylic acid L-alanylamide

EXAMPLE 48

3-Hydroxy-4-(4-trifluoromethylbenzyloxy)pyridine-2-carboxylic acid L-alanylamide

EXAMPLE 49

3-Hydroxy-4-(3-trifluoromethylbenzyloxy)pyridine-2-carboxylic acid L-alanylamide

EXAMPLE 50

3-Hydroxy-4-(4-trifluoromethoxybenzyloxy)pyridine-2-carboxylic acid L-alanylamide

EXAMPLE 51

4-(3,5-Bis(trifluoromethyl)benzyloxy)-3-hydroxypyridine-2-carboxylic acid L-alanylamide

EXAMPLE 52

4-(3,5-Dichlorobenzyloxy)-3-hydroxypyridine-2-carboxylic acid L-alanylamide

EXAMPLE 53

3-Hydroxy-4-(2,2,2-trifluoroethyloxy)pyridine-2-carboxylic acid L-alanylamide

EXAMPLE 54

3-Hydroxy-4-(2,2,3,3,3-pentafluoropropyloxy)pyridine-2-carboxylic acid L-alanylamide

EXAMPLE 55

4-(2,2,3,3,4,4,4-Heptafluorobutyloxy)-3-hydroxypyridine-2-carboxylic acid L-alanylamide

EXAMPLE 56

3-Hydroxy-4-(2,2,3,3-tetrafluoropropyloxy)pyridine-2-carboxylic acid L-alanylamide

EXAMPLE 57

4-Ethyloxy-3-hydroxypyridine-2-carboxylic acid L-phenylalanylamide

EXAMPLE 58

4-Butyloxy-3-hydroxypyridine-2-carboxylic acid L-phenylalanylamide

EXAMPLE 59

3-Hydroxy-4-propyloxypyridine-2-carboxylic acid L-phenylalanylamide

EXAMPLE 60

3-Hydroxy-4-(2-propyloxy)pyridine-2-carboxylic acid L-phenylalanylamide

EXAMPLE 61

3-Hydroxy-4-(2-methylpropyloxy)pyridine-2-carboxylic acid L-phenylalanylamide

EXAMPLE 62

3-Hydroxy-4-pentyloxypyridine-2-carboxylic acid L-phenylalanylamide

EXAMPLE 63

3-Hydroxy-4-(3-methylbutyloxy)pyridine-2-carboxylic acid L-leucylamide

EXAMPLE 64

4-(2-Ethylbutyloxy)-3-hydroxypyridine-2-carboxylic acid L-leucylamide

EXAMPLE 65

4-(2-Cyclohexylethyloxy)3-hydroxypyridine-2-carboxylic acid L-leucylamide

EXAMPLE 66

4-(Cyclohexylmethyloxy)-3-hydroxypyridine-2-carboxylic acid L-leucylamide

EXAMPLE 67

4-Cyclohexyloxy-3-hydroxypyridine-2-carboxylic acid L-leucylamide

EXAMPLE 68
3-Hydroxy-4-(3-methoxypropyloxy)pyridine-2-carboxylic acid L-leucylamide

EXAMPLE 69
3-Hydroxy-4-(2-phenoxyethloxy)pyridine-2-carboxylic acid L-leucylamide

EXAMPLE 70
4-Ethyloxy-3-hydroxypyridine-2-carboxylic acid D-alanylamide

EXAMPLE 71
4-Butyloxy-3-hydroxypyridine-2-carboxylic acid D-alanylamide

EXAMPLE 72
3-Hydroxy-4-propyloxypyridine-2-carboxylic acid D-alanylamide

EXAMPLE 73
3-Hydroxy-4-(2-propyloxy)pyridine-2-carboxylic acid D-alanylamide

EXAMPLE 74
3-Hydroxy-4-(2-methylpropyloxy)pyridine-2-carboxylic acid D-phenylalanylamide

EXAMPLE 75
3-Hydroxy-4-pentyloxypryidine-2-carboxylic acid D-phenylalanylamide

EXAMPLE 76
3-Hydroxy-4-(3-methylbutyloxy)pyridine-2-carboxylic acid L-valylamide

EXAMPLE 77
4-(2-Ethylbutyloxy)-3-hydroxypyridine-2-carboxylic acid L-valylamide

EXAMPLE 78
4-(2-Cyclohexylethyloxy)-3-hydroxypyridine-2-carboxylic acid L-valylamide

EXAMPLE 79
4-(Cyclohexylmethyloxy)-3-hydroxypyridine-2-carboxylic acid L-serylamide

EXAMPLE 80
4-Cyclohexylmethyloxy-3-hydroxypyridine-2-carboxylic acid L-norleucylamide

EXAMPLE 81
3-Hydroxy-4-(3-methoxypropyloxy)pyridine-2-carboxylic acid D-alanylamide

EXAMPLE 82
3-Hydroxy-4-(2-phenoxyethyloxy)pyridine-2-carboxylic acid D-alanylamide

EXAMPLE 83
6-Ethyloxy-3-hydroxypyridine-2-carboxylic acid glycylamide

EXAMPLE 84
6-Butyloxy-3-hydroxypyridine-2-carboxylic acid glycylamide

EXAMPLE 85
3-Hydroxy-6-propyloxypyridine-2-carboxylic acid glycylamide

EXAMPLE 86
3-Hydroxy-6-(2-propyloxy)pyridine-2-carboxylic acid glycylamide

EXAMPLE 87
3-Hydroxy-6-(2-methylpropyloxy)pyridine-2-carboxylic acid glycylamide

EXAMPLE 88
3-Hydroxy-6-pentyloxypyridine-2-carboxylic acid glycylamide

EXAMPLE 89
3-Hydroxy-6-(3-methylbutyloxy)pyridine-2-carboxylic acid glycylamide

EXAMPLE 90
6-(2-Ethylbutyloxy)-3-hydroxypyridine-2-carboxylic acid glycylamide

EXAMPLE 91
6-(2-Cyclohexylethyloxy)-3-hydroxypyridine-2-carboxylic acid L-alanylamide

EXAMPLE 92
6-(Cyclohexylmethyloxy)-3-hydroxypyridine-2-carboxylic acid glycylamide

EXAMPLE 93
6-Cyclohexyloxy-3-hydroxypyridine-2-carboxylic acid glycylamide

EXAMPLE 94
3-Hydroxy-6-(3-methoxypropyloxy)pyridine-2-carboxylic acid glycylamide

EXAMPLE 95
3-Hydroxy-6-(2-phenoxyethyloxy)pyridine-2-carboxylic acid glycylamide

EXAMPLE 96
6-Benzyloxy-3-hydroxypyridine-2-carboxylic acid glycylamide

EXAMPLE 97
6-(4-Chlorobenzyloxy)-3-hydroxypyridine-2-carboxylic acid glycylamide

EXAMPLE 98

6-(4-Fluorobenzyloxy)-3-hydroxypyridine-2-carboxylic acid glycylamide

EXAMPLE 99

3-Hydroxy-6-(2,2,2-trifluoroethyloxy)pyridine-2-carboxylic acid glycylamide

EXAMPLE 100

6-(2,2,3,3,4,4,4-Heptafluorobutyloxy)-3-hydroxypyridine-2-carboxylic acid glycylamide

EXAMPLE 101

3-Hydroxy-4-morpholinylpyridine-2-carboxylic acid glycylamide

EXAMPLE 102

3-Hydroxy-4-piperidylpyridine-2-carboxylic acid glycylamide

EXAMPLE 103

3-Hydroxy-4-pyrrolidinylpyridine-2-carboxylic acid glycylamide

EXAMPLE 104

4-Dimethylamino-3-hydroxypyridine-2-carboxylic acid glycylamide

EXAMPLE 105

5-Chloro-3-hydroxypyridine-2-carboxylic acid glycylamide

EXAMPLE 106

5-Cyano-3-hydroxypyridine-2-carboxylic acid glycylamide

EXAMPLE 107

3-Hydroxy-6-piperidylpyridine-2-carboxylic acid glycylamide

EXAMPLE 108

3-Hydroxy-6-morpholinylpyridine-2-carboxylic acid glycylamide

EXAMPLE 109

5-Carboxy-3-hydroxypyridine-2-carboxylic acid N-(carboxymethyl)amide

EXAMPLE 110

5-((1-Hexyloxy)carbonyl)-3-hydroxypyridine-2-carboxylic acid N-(carboxymethyl)amide

EXAMPLE 111

N-(3-Hydroxy-1-oxypyridine-2-carbonyl)glycine a) N-(3-Hydroxypyridine-2-carbonyl)glycine methyl ester 3-Hydroxypyridine-2-carboxylic acid (6.96 g, 50 mmol), 6.28 g of glycine methyl ester hydrochloride, 6.4 ml of N-ethylmorpholine and 13.53 g of 1-hydroxy-1H-benzotriazole were suspended in 300 ml of anhydrous dichloromethane and a solution of 10.83 g of DCC (=N,N'-dicyclohexylcarbodiimide) in 50 ml of dichloromethane was added to this suspension at 0° C. After 12 hours, the mixture was filtered and the filtrate was washed with water and with a saturated aqueous solution of NaHCO$_3$. Drying and concentrating yielded 7.33 g (70%) of N-(3-Hydroxypyridine-2-carbonyl)glycine methyl ester, m.p. 59°–61° C. (ethyl acetate/heptane), cf. example 1c) as well.

b) N-(3-hydroxy-1-oxypyridine-2-carbonyl)glycine methyl ester

N-(3-Hydroxy-2-carbonyl)glycine methyl ester (7.33 g, 34.9 mmol) were dissolved in 200 ml of dichloromethane and 12.42 g (72 mmol) of m-chloroperbenzoic acid were added to this solution. After 24 hours, the mixture was filtered. The filtrate was washed with water and with NaHCO$_3$ solution and concentrated. Chromatography of the residue using ethyl acetate/heptane (3:1) yielded 0.8 g (10%) of N-(3-hydroxy-1-oxypyridine-2-carbonyl)glycine methyl ester in the form of colourless crystals; m.p. 126°–128° C.

c) The title compound was obtained by dissolving N-(3-hydroxy-1-oxypyridine-2-carbonyl)glycine methyl ester (0.2 g, 0.9 mmol) in 5 ml of tetrahydrofuran and 10 ml of ethanol and adding 1.5 ml of a 1N aqueous solution of sodium hydroxide. After 4 hours, the mixture was concentrated in vacuo and the residue was taken up in 10 ml of water; the organic phase was extracted with dichloromethane. The aqueous phase was carefully acidified to pH 3 using hydrochloric acid and cooled. This resulted in the title compound in the form of colourless crystals (0.078 g, 42%). m.p. 186° C. (from aqueous hydrochloric acid).

EXAMPLE 112

3-Mercaptopyridine-2-carboxylic acid N-(carboxymethyl)amide a) 3-Mercaptopyridine-2-carboxylic acid was prepared in accordance with E. Sucharda, Cz. Troszkiewiczówna, Roczniki Chemiji 1932, 493.

b) 3-Mercaptopyridine-2-carboxylic acid N-((methoxycarbonyl)methyl)amide 1.69 g of 3-mercaptopyridine-2-carboxylic acid were dissolved in 20 ml of DMF and 7.5 ml of N-ethylmorpholine, 1.7 g of 1-hydroxy-1H-benzotriazole, 5 g of N-cyclohexyl-N'-(2-morpholinoethyl)-carbodiimide methyl-p-toluenesulfonate and 4.3 g of glycine methyl ester hydrochloride were added successively at room temperature and whilst stirring. After having been stirred for 12 hours, the mixture was partitioned between a saturated aqueous solution of ammonium chloride and dichloromethane and the organic phase was dried and concentrated by evaporation; the residue was purified by chromatography on silica gel (eluent: ethyl acetate/heptane); yield, 0.65 g of colourless crystals of m.p. 178°–179° C. (ethyl acetate/heptane).

c) 226 mg of the above compound were dissolved in 20 ml of 1,4-dioxane and 1.1 ml of a 1M aqueous solution of LiOH was added. After stirring at room temperature for several hours, the mixture was acidified with acetic acid and extracted several times with dichloromethane; the organic phases were dried and concentrated by evaporation. The residue was purified by chromatography on silica gel (eluent: ethyl acetate/acetic acid). Yield, 25 mg of colourless crystals, m.p. 252°–254° C. (from 2-propanol).

EXAMPLE 113

3-Hydroxyquinoline-2-carboxylic acid N-(carboxymethyl)amide a) 3-(2-Nitrobenzoyl)acetylacetone was obtained from acetylacetone and 2-nitrobenzoyl chloride, m.p. 69° C.; cf. J. Pract. Chem. 1987, 329, p. 1063, 29% yield.

b) 2-acetyl-3-hydroxyquinoline was obtained, under basic conditions (KOH/water, Smiles rearrangement), from the product a), m.p. 105° C.; cf. J. Chem. Soc. Chem. Comm. 1975, 782; 53% yield.

c) 2-acetyl-3-benzyloxyquinoline was obtained from the product b) using benzyl bromide (potassium carbonate/acetone), 52% yield, $^1$H-NMR (CDCl$_3$): δ=2.89 (s, 3H), 5.25 (s, 2H), 7.38 (m, 3H), 7.58 (m, 5H), 7.70 (m, 1H), 8.08 (m, 1H).

d) 3-benzyloxyquinoline-2-carboxylic acid was obtained from the product c) using potassium hypochlorite (dioxane/water), oily crude product, 47% yield, $^1$H-NMR (CDCl$_3$): δ=5.40 (s, 2H), 7.40 (m, 3H), 7.63 (m, 4H), 7.75 (m, 2H), 8.07 (m, 1H).

e) 3-benzyloxyquinoline-2-carboxylic acid N-((benzyloxycarbonyl)methyl)amide was obtained from the product d) using triethylamine/ethyl chloroformate (mixed anhydride method) and glycine benzyl ester tosylate, oily crude product, 64% yield, $^1$H-NMR (CDCl$_3$): δ=4.40 (d, 2H), 5.35 (s, 2H), 5.35 (s, 2H), 7.10 to 7.75 (m, 14H), 8.10 (m, 1H), 7.28 (t, 1H).

f) The title compound was obtained by hydrogenating the product e) in a hydrogenation vessel in methanol containing Pd/C (10%), m.p. 191° C. (from aqueous hydrochloric acid), 40% yield.

The following examples were prepared in analogy with example 113:

EXAMPLE 114
N-(3-Hydroxy-6-methoxyquinoline-1-carbonyl)glycine

EXAMPLE 115
N-(6-Ethyloxy-3-hydroxyquinoline-2-carbonyl)glycine

EXAMPLE 116
N-(6-(1-Butyloxy)-3-hydroxyquinoline-2-carbonyl)glycine

EXAMPLE 117
N-(6-(1-Hexyloxy)-3-hydroxyquinoline-2-carbonyl)glycine

EXAMPLE 118
N-(3-Hydroxy-6-(1-octyloxy)quinoline-2-carbonyl)glycine

EXAMPLE 119
N-(6-(1-Decyloxy)-3-hydroxyquinoline-2-carbonyl)glycine

EXAMPLE 120
N-(3-Hydroxy-6-((2,2,2-trifluoroethyl)oxy)quinoline-2-carbonyl)glycine

EXAMPLE 121
N-(3-Hydroxy-6-((2,2,3,3,3-pentafluoropropyl)oxy)quinoline-2-carbonyl)glycine

EXAMPLE 122
N-(6-((2,2,3,3,4,4,4-Heptafluorobutyl)oxy)-3-hydroxyquinoline-2-carbonyl)glycine

EXAMPLE 123
N-(6-Chloro-3-hydroxyquinoline-2-carbonyl)glycine

EXAMPLE 124
N-(6-Bromo-3-hydroxyquinoline-2-carbonyl)glycine

EXAMPLE 125
N-(3-Hydroxy-6-(4-phenylsulfonyl)quinoline-2-carbonyl)glycine

EXAMPLE 126
N-(6-((4-Fluorophenyl)sulfonyl)-3-hydroxyquinoline-2-carbonyl)glycine

EXAMPLE 127
N-(6-Benzyloxy-3-hydroxyquinoline-2-carbonyl)glycine

EXAMPLE 128
N-(6-(4-Fluorobenzyloxy)-3-hydroxyquinoline-2-carbonyl)glycine

EXAMPLE 129
N-(7-Butyloxy-3-hydroxyquinoline-2-carbonyl)glycine

EXAMPLE 130
N-(7-Benzyloxy-3-hydroxyquinoline-2-carbonyl)glycine

EXAMPLE 131
N-(6-(cis-3-Hexenyl-1-oxy)-3-hydroxyquinoline-2-carbonyl)glycine

EXAMPLE 132
N-(6-(trans-3-Hexenyl-1-oxy)-3-hydroxyquinoline-2-carbonyl)glycine

We claim:

1. A compound of the formula I

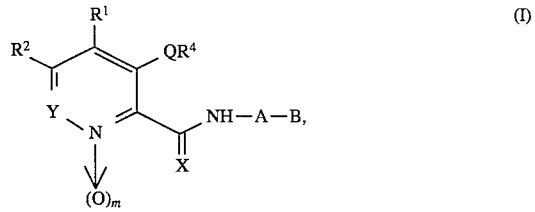

in which

Q is O or S,

X is O or S,

Y is CR$^3$, m is 0 or 1,

A is (C$_1$–C$_4$)-alkylene, which is optionally substituted by:
one or two substituents selected from the group halogen, cyano, nitro, trifluoromethyl, (C$_1$–C$_6$)-alkyl, (C$_1$–C$_6$)-hydroxyalkyl, (C$_1$–C$_6$)-alkoxy, —O—[CH$_2$]$_x$—C$_f$H$_{(2f+1-g)}$Hal$_g$, (C$_1$–C$_6$)-alkylmercapto, (C$_1$–C$_6$)-alkylsulfinyl, (C$_1$–C$_6$)-alkylsulfonyl, (C$_1$–C$_6$)-alkylcarbonyl, (C$_1$–C$_6$)-alkoxycarbonyl, carbamoyl, N-(C$_1$–C$_4$)-alkylcarbamoyl, N,N-di-(C$_1$–C$_4$)-alkylcarbamoyl, (C$_1$–C$_6$)-alkylcarbonyloxy, (C$_3$–C$_8$)-cycloalkyl, phenyl, benzyl, phenoxy, benzyloxy, anilino, N-methylanilino, phenylmercapto, phenylsulfonyl, phenylsulfinyl, sulfamoyl, N-(C$_1$–C$_4$)-alkylsulfamoyl and N,N-di-(C$_1$–C$_4$)-alkylsulfamoyl; or a $(C_6-C_{12})$-aryloxy, $(C_7-C_{11})$-aralkyloxy, $(C_6-C_{12})$-aryl or $(C_7-C_{11})$-aralkyl radical which carries in the aryl moiety 1, 2, 3, 4 or 5 identical or different substituents selected from the group halogen, cyano, nitro, trifluoro-methyl, $(C_1-C_6)$-alkyl, $(C_1-C_6)$alkoxy, —O—$[CH_2]_x$—$C_fH_{(2f+1-g)}Hal_g$, $(C_1-C_6)$-alkylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, N-$(C_1-C_4)$-alkylcarbamoyl, N,N-di-$(C_1-C_4)$-alkylcarbamoyl, $(C_1-C_6)$-alkylcarbonyloxy, $(C_3-C_8)$-cycloalkyl, sulfamoyl, N-$(C_1-C_4)$-alkylsulfamoyl and N,N-di-$(C_1-C_4)$-alkylsulfamoyl; or alternatively A is —$CHR^5$—, where $R^5$ differs from said substituent recited above for A and is a substituent of the α-carbon atom of an α-amino acid, said amino acid being a natural L-amino acid or its D-isomer, with the proviso that $R^5$ cannot be —$CH_2SH$;

B is selected from the group —$CO_2H$, —CONHCOR'", —CONHSOR'", $CONHSO_2R'''$, —$NHSO_2CF_3$, tetrazolyl, imidazolyl and 3-hydroxyisoxazolyl, or $(C_1-C_4)$-alkyl, optionally monosubstituted by $(C_6-C_{12})$-aryl, heteroaryl, OH, SH, $(C_1-C_4)$-alkyl, $(C_1-C_4)$-alkoxy, $(C_1-C_4)$-thioalkyl, $(C_1-C_4)$-sulfinyl, $(C_1-C_4)$-sulfonyl, $CF_3$, Cl, Br, F, I, $NO_2$, —COOH, $(C_2-C_5)$-alkoxycarbonyl, $NH_2$, mono-$(C_1-C_4$-alkyl)-amino, di-$(C_1-C_4$-alkyl)-amino or $(C_1-C_4)$-perfluoroalkyl;

$R^1$, $R^2$ and $R^3$ are identical or different and are selected from hydrogen, hydroxyl, halogen, cyano, trifluoromethyl, nitro, carboxyl, $(C_1-C_{20})$-alkyl, $(C_3-C_8)$-cycloalkyl, $(C_3-C_8)$-cycloalkyl-$(C_1-C_{12})$-alkyl, $(C_3-C_8)$-cycloalkoxy, $(C_3-C_8)$-cycloalkyl-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_8)$-alkyl-$(C_1-C_6)$-alkoxy, $(C_3-C_8)$-cycloalkyl-$(C_1-C_8)$-alkoxy-$(C_1-C_6)$-alkyl, $(C_3-C_8)$-cycloalkyloxy-$(C_1-C_8)$-alkoxy-$(C_1-C_6)$-alkyl, $(C_3-C_8)$-cycloalkoxy-$(C_1-C_8)$-alkoxy-$(C_1-C_8)$-alkoxy, $(C_6-C_{12})$-aryl, $(C_7-C_{16})$-aralkyl, $(C_7-C_{16})$-aralkenyl, $(C_7-C_{16})$-aralkynyl, $(C_2-C_{20})$-alkenyl, $(C_2-C_{20})$-alkynyl, $(C_1-C_{20})$-alkoxy, $(C_2-C_{20})$-alkenyloxy, $(C_2-C_{20})$-alkynyloxy, retinyloxy, $(C_1-C_{20})$-alkoxy-$(C_1-C_{12})$-alkyl, $(C_1-C_{12})$-alkoxy-$(C_1-C_{12})$-alkoxy, $(C_1-C_{12})$-alkoxy-$(C_1-C_8)$-alkoxy-$(C_1-C_8)$-alkyl, $(C_6-C_{12})$-aryloxy, $(C_7-C_{16})$-aralkyloxy, $(C_6-C_{12})$-aryloxy-$(C_1-C_6)$-alkoxy, $(C_7-C_{16})$-aralkoxy-$(C_1-C_6)$-alkoxy, $(C_1-C_{16})$-hydroxyalkyl, $(C_6-C_{16})$-aryloxy-$(C_1-C_8)$-alkyl, $(C_7-C_{16})$-aralkoxy-$(C_1-C_8)$-alkyl, $(C_6-C_{12})$-aryloxy-$(C_1-C_8)$-alkoxy-$(C_1-C_6)$-alkyl, $(C_7-C_{12})$-aralkyloxy-$(C_1-C_8)$-alkoxy-$(C_1-C_6)$-alkyl, $(C_2-C_{20})$-alkenyloxy-$(C_1-C_6)$-alkyl, $(C_2-C_{20})$-alkynyloxy-$(C_1-C_6)$-alkyl, retinyloxy-$(C_1-C_6)$-alkyl, —O—$[CH_2]_x$—$C_fH_{(2f+1-g)}Hal_g$, $(C_1-C_{20})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_2-C_{20})$-alkenylcarbonyl, $(C_2-C_{20})$-alkynylcarbonyl, $(C_1-C_{20})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{20})$-alkenyloxycarbonyl, retinyloxycarbonyl, $(C_2-C_{20})$-alkynyloxycarbonyl, $C_6-C_{12}$-aryloxy-$(C_1-C_6)$-alkoxycarbonyl, $(C_7-C_{16})$-aralkoxy-$(C_1-C_6)$-alkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N-$(C_1-C_{12})$-alkylcarbamoyl, N,N-di$(C_1-C_{12})$-alkylcarbamoyl, N-$(C_3-C_8)$-cycloalkylcarbamoyl, N,N-dicylco-$(C_3-C_8)$-alkylcarbamoyl, N-$(C_1-C_{10})$-alkyl-N-$(C_3-C_8)$-cycloalkylcarbamoyl, N-$((C_3-C_8)$-cycloalkyl-$(C_1-C_6)$-alkyl)carbamoyl, N-$(C_1-C_6)$-alkyl-N-$((C_3-C_8)$-cycloalkyl-$(C_1-C_6)$alkyl)carbamoyl, N-(+)-dehydroabietylcarbamoyl, N-$(C_1-C_6)$-alkyl-N-(+)-dehydroabietylcarbamoyl,N-$(C_6-C_{12})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1C_{18})$-alkoxy-$(C_1-C_{10})$-alkyl)carbamoyl,N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{12})$-aryloxy-$(C_1-C_{10})$-alkyl)carbamoyl, N-$((C_1-C_{10})$-alkyl-N-$((C_7-C_{16})$-aralkyloxy-$(C_1-C_{10})$-alkyl)carbamoyl, or $CON(CH_2)_h$, in which a $CH_2$ group can be replaced by O, S, N-$(C_1-C_8)$-alkylimino, N-$(C_3-C_8)$-cycloalkylimino, N-$(C_3-C_8)$-cycloalkyl-$(C_1-C_4)$-alkylimino, N-$(C_6-C_{12})$-arylimino, N-$(C_7-C_{16})$-aralkylimino, N-$(C_1-C_4)$-alkoxy-$(C_1-C_6)$-alkylimino, and a carbamoyl radical of the formula J

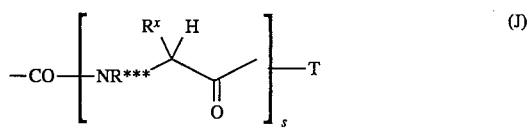

in which $R^x$ is the substituent of an L- or D- α-amino acid, s is 1, 2, 3, 4 or 5, and T is OH, OR or NR*R**, where R*, R and R* are identical or different and are hydrogen, $(C_6-C_{12})$-aryl, $(C_7-C_{11})$-aralkyl, $(C_1-C_8)$-alkyl, $(C_3-C_8)$-cycloalkyl, (+)-dehydroabietyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkylcarbonyl, optionally substituted $(C_7-C_{16})$-aralkylcarbonyl or optionally substituted $(C_6-C_{12})$-arylcarbonyl, or R* and R** are together —$[CH_2]_h$, in which a $CH_2$ group can be replaced by O, S, SO, $SO_2$, N-acylamino, N-$(C_1-C_{10})$-alkoxycarbonylimino, N-$(C_1-C_8)$-alkylimino, N-$(C_3-C_8)$-cycloalkylimino, N-$(C_3-C_8)$-cycloalkyl-$(C_1-C_4)$-alkylimino, N-$(C_6-C_{12})$-arylimino, N-$(C_7-C_{16})$-aralkylimino or N-$(C_1-C_4)$-alkoxy-$(C_1-C_6)$-alkylimino, and further wherein $R^1$, $R^2$, and $R^3$ are identical or different and are further selected from carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{12})$-arylcarbamoyloxy, N-$(C_7-C_{16})$-aralkyl-carbamoyloxy, N-$(C_1-C_{10})$-alkyl-N-$(C_6-C_{12})$-arylcarbamoyloxy, N-($C_1$-$C_{10}$)-alkyl-N-($C_7$-$C_{16}$)-aralkylcarbamoyloxy, N-(($C_1$-$C_{10}$)-alkyl)carbamoyloxy, N-(($C_6$-$C_{12}$)-aryloxy-($C_1$-$C_{10}$)-alkyl)carbamoyloxy, N-(($C_7$-$C_{16}$)-aralkyloxy-($C_1$-$C_{10}$)-alkyl)carbamoyloxy, N-($C_1$-$C_{10}$)-alkyl-N-(($C_1$-$C_{10}$)-alkoxy-($C_1$-$C_{10}$)-alkyl)carbamoyloxy, N-($C_1$-$C_{10}$)-alkyl-N-(($C_6$-$C_{12}$)-aryloxy-($C_1$-$C_{10}$)-alkyl) carbamoyloxy, N-($C_1$-$C_{10}$)-alkyl-N-(($C_7$-$C_{16}$)-aralkyloxy-($C_1$-$C_{10}$)-alkyl)carbamoyloxy, $NR^yR^z$, wherein $R^y$ and $R^z$ are independently selected from hydrogen, ($C_1$-$C_{12}$)-alkyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_3$-$C_{10}$)-cycloalkyl, ($C_3$-$C_{12}$)-alkenyl, ($C_3$-$C_{12}$)-alkynyl, ($C_6$-$C_{12}$)-aryl, ($C_7$-$C_{11}$)-aralkyl, ($C_1$-$C_{12}$)-alkoxy, ($C_7$-$C_{12}$)aralkoxy, ($C_1$-$C_{12}$)-alkylcarbonyl, ($C_3$-$C_8$)-cycloalkylcarbonyl, ($C_6$-$C_{12}$) arylcarbonyl, and ($C_7$-$C_{16}$)-aralkylcarbonyl, or further wherein $R^y$ and $R^z$ together are —[$CH_2$]$_h$ in which a $CH_2$ group can be replaced by O, S, N-($C_1$-$C_4$)-alkylcarbonylimino or N-($C_1$-$C_4$)-alkoxycarbonylimino, and further wherein $R^1$, $R^2$, and $R^3$ are identical or different and are further selected from ($C_1$-$C_{12}$)-alkylcarbonylamino-($C_1$-$C_8$)-alkyl, ($C_3$-$C_8$)-cycloalkylcarbonylamino-($C_1$-$C_8$)-alkyl, ($C_6$-$C_{12}$)-arylcarbonylamino-($C_1$-$C_8$)-alkyl, ($C_7$-$C_{16}$)-aralkylcarbonylamino-($C_1$-$C_8$)-alkyl, amino-($C_1$-$C_{10}$)-alkyl, N-($C_1$-$C_{10}$)-alkylamino-($C_1$-$C_{10}$)-alkyl, N,N-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, ($C_1$-$C_{12}$)-alkylmercapto-($C_1$-$C_6$)-alkyl, ($C_1$-$C_{12}$)-alkylsulfinyl-($C_1$-$C_6$)-alkyl, ($C_1$-$C_{12}$)-alkylsulfonyl-($C_1$-$C_6$)-alkyl, ($C_6$-$C_{12}$)-arylmercapto-($C_1$-$C_6$)-alkyl, ($C_6$-$C_{12}$)-arylsulfinyl-($C_1$-$C_6$)-alkyl, $C_6$-$C_{12}$-arylsulfonyl-($C_1$-$C_6$)-alkyl, ($C_7$-$C_{16}$)-aralkylmercapto-($C_1$-$C_6$)-alkyl, ($C_7$-$C_{16}$)-aralkylsulfinyl-($C_1$-$C_6$)-alkyl, ($C_7$-$C_{16}$)-aralkylsulfonyl-($C_1$-$C_6$)-alkyl, sulfamoyl, N-($C_1$-$C_{10}$)-alkylsulfamoyl, N,N-di-($C_1$-$C_{10}$)-alkylsulfamoyl, ($C_3$-$C_8$)-cycloalkylsulfamoyl, N-($C_6$-$C_{12}$)-arylsulfamoyl, N-($C_7$-$C_{16}$)-aralkylsulfamoyl, N-($C_1$-$C_{10}$)-alkyl-N-($C_6$-$C_{12}$)-arylsulfamoyl, N-($C_1$-$C_{10}$)-alkyl-N-($C_7$-$C_{16}$)-aralkylsulfamoyl, ($C_1$-$C_{10}$)-alkylsulfonamido, N-(($C_1$-$C_{10}$)alkyl)-($C_1$-$C_{10}$)alkylsulfonamido, ($C_7$-$C_{16}$)-aralkylsulfonamido and N-(($C_1$-$C_{10}$)-alkyl)-($C_7$-$C_{16}$)-aralkylsulfonamido, where the radicals which contain an aryl radical or moiety may be substituted on the aryl by from 1 to 5 identical or different radicals selected from the group:

hydroxyl, halogen, cyano, trifluoromethyl, nitro, carboxyl, ($C_1$-$C_{16}$)-alkyl, ($C_3$-$C_8$)-cycloalkyl, ($C_3$-$C_8$)-cycloalkyl-($C_1$-$C_{12}$)-alkyl, ($C_3$-$C_8$)-cycloalkoxy, ($C_3$-$C_8$)-cycloalkyl-($C_1$-$C_{12}$)-alkoxy, ($C_3$-$C_8$)-cycloalkyloxy-($C_1$-$C_{12}$)-alkyl, ($C_3$-$C_8$)-cycloalkyloxy-($C_1$-$C_{12}$)-alkoxy, ($C_3$-$C_8$)-cycloalkyl-($C_1$-$C_8$)-alkyl-($C_1$-$C_6$)-alkoxy, ($C_3$-$C_8$)-cycloalkyl-($C_1$-$C_8$)-alkoxy-($C_1$-$C_6$)-alkyl, ($C_3$-$C_8$)-cycloalkyloxy-($C_1$-$C_8$)-alkoxy-($C_1$-$C_6$)-alkyl, ($C_3$-$C_8$)-cycloalkoxy-($C_1$-$C_8$)-alkoxy-($C_1$-$C_8$)-alkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_2$-$C_{16}$)-alkenyloxy, ($C_1$-$C_{12}$)-alkoxy-($C_1$-$C_{12}$)-alkyl, ($C_1$-$C_{12}$)-alkoxy-($C_1$-$C_{12}$)-alkoxy, ($C_1$-$C_{12}$)-alkoxy-($C_1$-$C_8$)-alkoxy-($C_1$-$C_8$)-alkyl, ($C_6$-$C_{12}$)-aryloxy, ($C_7$-$C_{16}$)-aralkyloxy, ($C_6$-$C_{12}$)-aryloxy-($C_1$-$C_6$)-alkoxy, ($C_7$-$C_{16}$)-aralkoxy-($C_1$-$C_6$)-alkoxy, ($C_1$-$C_8$)-hydroxyalkyl, ($C_6$-$C_{16}$)-aryloxy-($C_1$-$C_8$)-alkyl, ($C_7$-$C_{16}$)-aralkoxy-($C_1$-$C_8$)-alkyl, ($C_6$-$C_{12}$)-aryloxy-($C_1$-$C_8$)-alkoxy-($C_1$-$C_6$)-alkyl, ($C_7$-$C_{12}$)-aralkyloxy-($C_1$-$C_8$)-alkoxy-($C_1$-$C_6$)-alkyl, —O—[$CH_2$]$_x$—$C_fH_{(2f+1-g)}F_g$—$OCF_2Cl$, —$OCF_2$—$CHFCl$, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, ($C_6$-$C_{12}$)-aryloxy-($C_1$-$C_6$)-alkoxycarbonyl, ($C_7$-$C_{16}$)-aralkoxy-($C_1$-$C_6$)-alkoxycarbonyl, ($C_3$-$C_8$)-cycloalkyl-($C_1$-$C_6$)-alkoxycarbonyl, ($C_3$-$C_8$)-cycloalkoxy-($C_1$-$C_6$)-alkoxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxy-carbonyloxy, carbamoyl, N-($C_1$-$C_{12}$)-alkylcarbamoyl, N,N-di-($C_1$-$C_{12}$)-alkylcarbamoyl, N-($C_3$-$C_8$)-cycloalkylcarbamoyl, N,N-dicyclo-($C_3$-$C_8$)-alkylcarbamoyl, N-($C_1$-$C_{10}$)-alkyl-N-($C_3$-$C_8$)-cycloalkylcarbamoyl, N-(($C_3$-$C_8$)-cycloalkyl-($C_1$-$C_6$)-alkyl)carbamoyl, N-($C_1$-$C_6$)-alkyl-N-($C_3$-$C_8$)-cycloalkyl-($C_1$-$C_6$)-alkyl)carbamoyl, N-(+)-dehydroabietylcarbamoyl, N-($C_1$-$C_6$)-alkyl-N-(+)-dehydroabietylcarbamoyl, N-($C_6$-$C_{12}$)-arylcarbamoyl, N-($C_7$-$C_{16}$)-aralkylcarbamoyl, N-($C_1$-$C_{10}$)-alkyl-N-($C_6$-$C_{16}$)arylcarbamoyl, N-($C_1$-$C_{10}$)-alkyl-N-($C_7$-$C_{16}$-aralkylcarbamoyl, N-(($C_1$-$C_{16}$)-alkoxy-($C_1$-$C_{10}$)alkyl)carbamoyl, N-(($C_6$-$C_{16}$)-aryloxy-($C_1$-$C_{10}$)alkyl)carbamoyl, N-(($C_7$-$C_{16}$)-aralkyloxy-($C_1$-$C_{10}$)alkyl)carbamoyl, N-($C_1$-$C_{10}$)-alkyl-N-(($C_1$-$C_{10}$)-alkoxy-($C_1$-$C_{10}$)-alkyl)carbamoyl, N-($C_1$-$C_{10}$)-alkyl-N-(($C_6$-$C_{12}$)-aryloxy($C_1$-$C_{10}$)alkyl)carbamoyl, N-($C_1$-$C_{10}$)-alkyl-N-(($C_7$-$C_{16}$)-aralkyloxy-($C_1$-$C_{10}$)alkyl)carbamoyl, CON($CH_2$)$_h$ in which a $CH_2$ group can be replaced by O, S, N-($C_1$-$C_8$)-alkylimino, N-($C_3$-$C_8$)cycloalkylimino, N-($C_3$-$C_8$)-cycloalkyl-($C_1$-$C_4$)alkylimino, N-($C_6$-$C_{12}$)-arylimino, N-($C_7$-$C_{16}$)-aralkylimino or N-($C_1$-$C_4$)-alkoxy-($C_1$-$C_6$)-alkylimino, carbamoyloxy, N-($C_1$-$C_{12}$)-alkylcarbamoyloxy, N,N-di-($C_1$-$C_{12}$)-alkylcarbamoyloxy, N-($C_3$-$C_8$)-cycloalkylcarbamoyloxy, N-($C_6$-$C_{16}$)-arylcarbamoyloxy, N-($C_7$-$C_{16}$)-aralkylcarbamoyloxy, N-($C_1$-$C_{10}$)-alkyl-N-($C_6$-$C_{12}$)arylcarbamoyloxy, N-($C_1$-$C_{10}$)-alkyl-N-($C_7$-$C_{16}$)-aralkylcarbamoyloxy, N-(($C_1$-$C_{10}$)alkyl)-carbamoyloxy, N-(($C_6$–$C_{12}$)-aryloxy-($C_1$–$C_{10}$)alkyl)carbamoyloxy, N-(($C_7$–$C_{16}$)-aralkyloxy-($C_1$–$C_{10}$)alkyl)carbamoyloxy, N-($C_1$–$C_{10}$)-alkyl-N-(($C_1$–$C_{10}$)-alkoxy-($C_1$–$C_{10}$)-alkyl)carbamoyloxy, N-($C_1$–$C_{10}$)-alkyl-N-(($C_6$–$C_{12}$)-aryloxy-($C_1$–$C_{10}$)-alkyl)carbamoyloxy, N-($C_1$–$C_{10}$)-alkyl-N-(($C_7$–$C_{16}$)-aralkyloxy-($C_1$–$C_{10}$)-alkyl)carbamoyloxy, $NR^yR^z$, wherein $R^y$ and $R^z$ are as defined above, ($C_1$–$C_{12}$)-alkylcarbonylamino-($C_1$–$C_8$)-alkyl, ($C_3$–$C_8$)-cycloalkylcarbonylamino-($C_1$–$C_8$)-alkyl, ($C_6$–$C_{12}$)-arylcarbonylamino-($C_1$–$C_8$)-alkyl, ($C_7$–$C_{16}$)-aralkylcarbonylamino-($C_1$–$C_8$)-alkyl, amino-($C_1$–$C_{10}$)-alkyl, N-($C_1$–$C_{10}$)-alkylamino-($C_1$–$C_{10}$)alkyl, N,N-di-($C_1$–$C_{10}$)alkylamino-($C_1$–$C_{10}$)alkyl, ($C_3$–$C_8$)-cycloalkylamino-($C_1$–$C_{10}$)-alkyl, ($C_1$–$C_{12}$)-alkylmercapto, ($C_1$–$C_{12}$)-alkylsulfinyl, ($C_1$–$C_{12}$)-alkylsulfonyl, ($C_6$–$C_{16}$)-arylmercapto, ($C_6$–$C_{16}$)-arylsulfinyl, ($C_6$–$C_{16}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, sulfamoyl, N-($C_1$–$C_4$)-alkylsulfamoyl, and N,N-di-($C_1$–$C_4$)-alkylsulfamoyl, or alternatively, in the case when said radicals which are aryl or which contain an aryl moiety are substituted by up to 3 of said radicals, then two adjacent carbon atoms of an aralkyloxy radical recited in the definition of $R^1$ and $R^3$ together carry at least one chain selected from —[$CH_2$—]$_n$ and —CH=CH—CH=CH—, where a $CH_2$ group of the chain is optionally replaced by O, S, SO, $SO_2$ or NR', and further wherein $R^1$, $R^2$, and $R^3$ are identical or different and are further selected from a radical of the formula Z:

$$-[CH_2]_v-[O]_w-[CH_2]_t-E, \quad (Z)$$

where E is a phenyl radical of the formula F

a heteroaryl radical or a ($C_3$–$C_8$)-cycloalkyl radical, where v is 0, 1, 2, 3, 4, 5 or 6, w is 0 or 1, and t is 0, 1, 2, or 3, with the restriction that v is not 0 if w is 1, and the further restriction that v, w, and t cannot simultaneously be 0 if E is the phenyl radical of formula F or is a cycloalkyl, and $R^6$, $R^7$, $R^8$, $R^9$ and $R^{10}$ are identical or different and are selected from hydrogen, halogen, cyano, nitro, trifluoromethyl, ($C_1$–$C_6$)-alkyl, ($C_3$–$C_8$)-cycloalkyl, ($C_1$–$C_6$)-alkoxy, —O—[$CH_2$]$_x$—$C_fH_{(2f+1-g)}F_g$, —$OCF_2Cl$, —O—$CF_2$—CHFCl, ($C_1$–$C_6$)-alkylmercapto, ($C_1$–$C_6$)-hydroxyalkyl, ($C_1$–$C_6$)-alkoxy-($C_1$–$C_6$)-alkoxy, ($C_1$–$C_6$)-alkoxy-($C_1$–$C_6$)-alkyl, ($C_1$–$C_6$)-alkylsulfinyl ($C_1$–$C_6$)-alkylsulfonyl, ($C_1$–$C_6$)-alkylcarbonyl, ($C_1$–$C_8$)-alkoxycarbonyl, carbamoyl, N-($C_1$–$C_8$)-alkylcarbamoyl, N,N-di-($C_1$–$C_8$)-alkylcarbamoyl, ($C_7$–$C_{11}$)-aralkylcarbamoyl optionally substituted by fluorine, chlorine, bromine, trifluoromethyl or ($C_1$–$C_6$)-alkoxy, N-($C_3$–$C_8$)-cycloalkylcarbamoyl, N-($C_3$–$C_8$)-cycloalkyl-($C_1$–$C_4$)-alkylcarbamoyl, ($C_1$–$C_6$)-alkylcarbonyloxy, phenyl, benzyl, phenoxy, benzyloxy, $NR^yR^z$, phenylmercapto, phenylsulfonyl, phenylsulfinyl, sulfamoyl,N-($C_1$–$C_8$)-alkylsulfamoyl and N,N-di-($C_1$–$C_8$)-alkylsulfamoyl, or $R^6$ and $R^7$, $R^7$ and $R^8$, $R^8$ and $R^9$, or $R^9$ and $R^{10}$ together are a chain —[$CH_2$]$_n$ or —CH=CH—CH=CH—, where a $CH_2$ group of the chain is optionally replaced by O, S, SO, $SO_2$ or NR', or, alternatively, wherein $R^2$ is as defined above and $R^1$ and $R^3$ are identical or different and are selected from a radical of the formula D:

$$OZ \quad (D),$$

in which Z is as previously defined, and if one of $R^1$ and $R^3$ is not (D), said one is as defined above, or, alternatively, $R^1$ is as defined above and $R^2$ and $R^3$ together with the atoms to which they are bonded form an aromatic or partially unsaturated ring in which one or two $CH_2$ groups of the partially unsaturated ring can be replaced by O, S, SO, $SO_2$ or NR', $R^1$ is hydrogen, ($C_6$–$C_{12}$)-aryl, ($C_1$–$C_8$)-alkyl, ($C_1$–$C_8$)-alkoxy-($C_1$–$C_8$)-alkyl, ($C_7$–$C_{12}$)-aralkoxy-($C_1$–$C_8$)-alkyl, ($C_6$–$C_{12}$)-aryloxy-($C_1$–$C_8$)-alkyl, ($C_1$–$C_{10}$)-alkylcarbonyl, ($C_7$–$C_{16}$)-aralkylcarbonyl or ($C_6$–$C_{12}$)-arylcarbonyl, $R^4$ is hydrogen, f is 1 to 8, g is 0 or 1 to (2f+1), n is 3 or 4, x is 0 to 3 and h is 3 to 7, or a physiologically active salt thereof or a prodrug of said compound of formula (I), wherein said prodrug differs from said compound of formula (I), with 3-hydroxypyridine-2-carboxylic acid N-(carboxymethyl)amide, 3-hydroxypyridine-2-carboxylic acid N-(carboxy-2-hydroxypropyl)amide, 3-hydroxypyridine-2-carboxylic acid-N-(glycyl ethyl ester)amide and 3-hydroxypyridine-2-carboxylic acid-N-(threonyl benzyl ester)amide being excluded.

2. A compound of the formula I as claimed in claim 1, in which

Q is O or S,

X is O,

Y is $CR^3$, m is 0 or 1,

A is ($C_1$–$C_3$)-alkylene, which is optionally substituted once by halogen, cyano, trifluoromethyl, ($C_1$–$C_6$)-alkyl, ($C_1$–$C_6$)-hydroxyalkyl, ($C_1$–$C_6$)-alkoxy or —O—[$CH_2$]$_x$—$C_fH_{(2f+1-g)}F_g$, or A is —$CHR^5$—, where $R^5$ differs from said substituent recited above for A and is a substituent of the α-carbon atom of an α-amino acid, said amino acid being a natural L-amino acid or its D-isomer, with the proviso that $R^5$ cannot be —$CH_2SH$, B is $CO_2H$, $R^2$ is hydrogen, ($C_1$–$C_{20}$)-alkyl, ($C_2$–$C_{20}$)-alkenyl, ($C_2$–$C_{20}$)-alkynyl, ($C_1$–$C_{20}$)-alkoxy, ($C_2$–$C_{20}$)-alkenyloxy, ($C_2$–$C_{20}$)-alknyloxy, retinyloxy, ($C_1$–$C_{20}$)-alkoxy-($C_1$–$C_3$)-alkyl, ($C_2$–$C_{20}$)-alkenyloxy-($C_1$–$C_3$)-alkyl, retinyloxy-($C_1$–$C_3$)-alkyl, ($C_2$–$C_{20}$)-alkynyloxy-($C_1$–$C_3$)-alkyl, halogen, cyano, trifluoromethyl, $(C_1-C_8)$-hydroxylalkyl, $(C_1-C_{20})$-alkylcarbonyl, $(C_7-C_{16})$-aralkylcarbonyl, $(C_6-C_{12})$-arylcarbonyl, $(C_6-C_{12})$-aryl, $(C_7-C_{16})$-aralkyl, —O—$[CH_2]_x$—$C_fH_{(2f+1-g)}F_g$, $NR^YR^Z$, $(C_1-C_{10})$-alkylmercapto, $(C_1-C_{10})$-alkylsulfinyl, $(C_1-C_{10})$-alkylsulfonyl, $(C_6-C_{12})$-arylmercapto, $(C_6-C_{12})$-arylsulfinyl, $(C_6-C_{12})$-arylsulfonyl, $(C_7-C_{12})$-aralkylmercapto, $(C_7-C_{12})$-aralkylsulfinyl, $(C_7-C_{12})$-aralkylsulfonyl, $(C_6-C_{12})$-aryloxy, $(C_7-C_{16})$-aralkyloxy, carboxyl, $(C_1-C_{20})$-alkoxycarbonyl, $(C_1-C_{12})$-alkoxy-$(C_1-C_{12})$-alkoxycarbonyl, $(C_6-C_{12})$-aryloxycarbonyl, $C_7-C_{16}$-aralkoxycarbonyl, $(C_3-C_8)$-cycloalkoxycarbonyl, $(C_2-C_{20})$-alkenyloxycarbonyl, retinyloxycaronyl, $(C_2-C_{20})$-alkynyloxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_6-C_{12})$-aryloxy-$(C_1-C_6)$-alkoxycarbonyl, $(C_7-C_{16})$-aralkoxy-$(C_1-C_6)$-alkoxycarbonyl, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N,N-dicyclo-$(C_3-C_8)$-alkylcarbamoyl, N-$(C_1-C_{10})$-alkyl-N-$(C_3-C_8)$-cycloalkylcarbamoyl, N-$(C_3-C_8)$-cycloalkyl-$(C_1-C_6)$-alkyl)carbamoyl, N-$(C_1-C_6)$-alkyl-N-$((C_3-C_8)$-cycloalkyl-$(C_1-C_6)$-alkyl)carbamoyl, N-(+)-dehydroabietylcarbamoyl, N-$(C_1-C_6)$-alkyl-N-(+)-dehydroabietylcarbamoyl, N-$(C_6-C_{12})$-arylcarbamoyl, N-$(C_7-C_{16})$-aralkylcarbamoyl, N-$(C_1-C_{10})$-alkyl-N-$(C_7-C_{16})$-aralkylcarbamoyl, N-$((C_1-C_{12})$-alkoxy-$(C_1-C_{10})$alkyl)carbamoyl, N-$((C_6-C_{16})$-aryloxy-$(C_1-C_{10})$alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{12})$-aryloxy$(C_1-C_{10})$alkyl)carbamoyl, N-$(C_1-C_{10})$-alkyl-N-$((C_7-C_{16})$-aralkyloxy-$(C_1-C_{10})$alkyl)carbamoyl or $CON(CH_2)_h$ in which a $CH_2$ group can be replaced by O, S, N-$(C_1-C_8)$-alkylimino, N-$(C_3-C_8)$cycloalkylimino, N-$(C_3-C_8)$-cycloalkyl-$(C_1-C_4)$alkylimino, N-$(C_6-C_{12})$-arylimino, N-$(C_7-C_{16})$-aralkylimino or N-$(C_1-C_4)$-alkoxy-$(C_1-C_6)$-alkylimino, where said radicals defined above for $R^2$ which contain an aryl group or moiety may be substituted on the aryl in the manner defined for $R^1$ and $R^3$ below.

$R^1$ and $R^3$ are identical or different and are hydrogen, halogen, $(C_1-C_{12})$-alkyl, $(C_1-C_{12})$-alkoxy, —O—$[CH_2]_x$—$C_fH_{(2f+1-g)}Hal_g$, $(C_1-C_{12})$-alkoxy-$(C_1-C_{12})$-alkyl-$(C_1-C_8)$-alkoxy-$(C_1-C_{12})$-alkoxy, $(C_1-C_{12})$-alkoxy-$(C_1-C_8)$-alkoxy-$(C_2-C_6)$-alkyl, $(C_7-C_{11})$-aralkyloxy, $(C_3-C_8)$-cycloalkyl, $(C_3-C_8)$-cycloalkyl-$(C_1-C_8)$-alkyl, $(C_3-C_8)$-cycloalkyloxy, $(C_3-C_8)$-cycloalkyl-$(C_1-C_8)$-alkoxy, $(C_3-C_8)$-cycloalkyloxy-$(C_1-C_8)$-alkyl, $(C_3-C_8)$-cycloalkyloxy-$(C_1-C_8)$-alkoxy, $(C_3-C_8)$-cycloalkyl-$(C_1-C_6)$-alkyl-$(C_1-C_6)$-alkoxy-$(C_3-C_8)$-cycloalkyl-$(C_1-C_6)$-alkoxy-$(C_1-C_6)$-alkyl, $(C_3-C_8)$-cycloalkoxy-$(C_1-C_6)$-alkoxy-$(C_1-C_6)$-alkyl, $NR^YR^Z$, $(C_1-C_8)$-alkylmercapto, $(C_1-C_8)$-alkylsulfinyl or $(C_1-C_8)$-alkylsulfonyl, $(C_6-C_{12})$-arylmercapto, $(C_6-C_{12})$-arylsulfinyl, $(C_6-C_{12})$-arysulfonyl, $(C_7-C_{12})$-aralkylmercapto, $(C_7-C_{11})$-aralkylsulfinyl, $(C_7-C_{11})$-aralkylsulfonyl, $(C_6-C_{12})$-aryloxy-$(C_1-C_6)$-alkyl, $(C_7-C_{11})$-aralkyloxy-$(C_1-C_6)$-alkyl, $(C_6-C_{12})$-aryloxy-$(C_1-C_6)$-alkoxy-$(C_1-C_6)$-alkyl, $(C_7-C_{11})$-aralkyloxy-$(C_1-C_6)$-alkoxy-$(C_1-C_6)$-alkyl, $(C_6-C_{12})$-aryloxy, $(C_7-C_{11})$-aralkyloxy, $(C_6-C_{12})$-aryloxy-$(C_1-C_6)$-alkoxy or $(C_7-C_{11})$-aralkoxy-$(C_1-C_6)$-alkoxy, where the radicals which contain an aryl radical or moiety may be substituted on the aryl by from 1 to 5 identical or different radicals selected from the group hydroxyl, halogen, cyano, nitro, trifluoromethyl, $(C_1-C_{16})$-alkyl, $(C_2-C_{16})$-alkenyl, $(C_1-C_6)$-hydroxyalkyl, $(C_1-C_{16})$-alkoxy, $(C_2-C_{16})$-alkenyloxy, —O—$[CH_2]_x$—$C_fH_{(2f+1-g)}F_g$, $OCF_2Cl$, —O—$CF_2$—$CHFCl$, $(C_1-C_6)$-alkylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, N-$(C_1-C_4)$-alkylcarbamoyl, N,N-di-$(C_1-C_4)$-alkylcarbamoyl, $(C_1-C_6)$-alkylcarbonyloxy, N-$(C_3-C_8)$-cycloalkylcarbamoyl, phenyl, benzyl, phenoxy, benzyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-alkyl-aralkylamino, N-alkyl-arylamino, $(C_1-C_{12})$-alkoxyamino, $(C_1-C_{12})$-alkoxy-N-$(C_1-C_{10})$-alkylamino, $(C_1-C_{12})$-alkylcarbonylamino, $(C_3-C_8)$-cycloalkylcarbonylamino, $(C_6-C_{12})$-arylcarbonylamino, $(C_7-C_{16})$-aralkylcarbonylamino, $(C_1-C_{12})$-alkylcarbonyl-N-$(C_1-C_{10})$-alkylamino, $(C_3-C_8)$-cycloalkylcarbonyl-N-$(C_1-C_{10})$-alkylamino, $(C_6-C_{12})$-arylcarbonyl-N-$(C_1-C_{10})$alkylamino, $(C_7-C_{11})$-aralkylcarbonyl-N-$(C_1-C_{10})$-alkylamino, phenylmercapto, phenylsulfinyl, phenylsulfonyl, sulfamoyl, N-$(C_1-C_4)$-alkylsulfamoyl and N,N-di-$(C_1-C_4)$-alkylsulfamoyl, or, alternatively, in the case when said aryl radical is substituted by up to 3 of said radicals, then two adjacent aromatic carbon atoms of an aralkyloxy radical recited in the definition of $R^1$ and $R^3$ together may carry a chain —$[CH_2]_n$ and/or —CH=CH—CH=CH—, where a $CH_2$ group of the chain is optionally replaced by O, S, SO, $SO_2$ or NR', wherein R' is as defined in claim 18 or alternatively wherein at least one of $R^1$ and $R^3$, which are identical or different, is selected from a radical of the formula D $$OZ \qquad (D),$$

where Z is as defined in claim 1 and wherein the other of $R^1$ of $R^3$ which is not D is as defined above, or, alternatively, $R^1$ is as defined above and $R^2$ and $R^3$ together form a chain $[CH_2]_o$, where o is 3, 4 or 5, or form, together with the pyridine carrying them, a quinoline ring of the formula 1a,

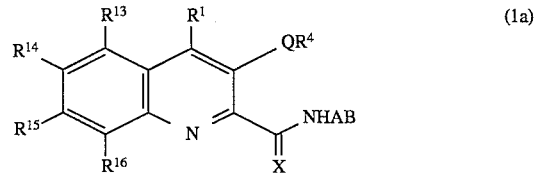

where $R^{13}$, $R^{14}$, $R^{15}$ and $R^{16}$ are independently hydrogen, $(C_1-C_{12})$-alkyl, $(C_2-C_{12})$-alkenyl, chlorine, fluorine, bromine, trifluoromethyl, $(C_1-C_{12})$-alkylsulfonyl, $(C_1-C_{12})$-alkylsulfinyl, phenylsulfonyl, phenylsulfinyl, where said radicals containing a phenyl radical or moiety may be substituted on the phenyl by fluorine, chlorine or $(C_1-C_5)$-alkoxy, and wherein $R^{13}$, $R^{14}$, $R^{15}$, and $R^{16}$ are further independently $(C_1-C_{10})$-alkoxy, —O—$[CH_2]_x$—$C_fH_{(2f+1-g)}$, $F_g$ or a radical of said formula D $R^4$ is hydrogen $R^Y$ and $R^Z$ are identical or different and are hydrogen, $(C_6-C_{12})$-aryl, $(C_1-C_{10})$-alkyl, $(C_3-C_{10})$-cycloalkyl, $(C_1-C_8)$-alkoxy-$(C_1-C_8)$-alkyl, $(C_7-C_{12})$-aralkyl-$(C_1-C_8)$-alkyl, $(C_6-C_{12})$-aryloxy-$(C_1-C_8)$-alkyl, $(C_1-C_{10})$-alkylcarbonyl, $(C_7-C_{16})$-aralkylcarbonyl or $(C_6-C_{12})$-arylcarbonyl, or alternatively $R^Y$ and $R^Z$ together are —$[CH_2]_h$— in which a $CH_2$ group can be replaced by O, S, N-$(C_1-C_4)$-alkylcarbonylimino or N-$(C_1-C_4)$-alkoxycarbonylimino, and f is to 1 to 8, g is 0 or 1 to (2f+1), h is 3 to 7, x is 0 to 3, and n is 3 or 4, or a physiologically active salt thereof, with 3-hydroxypyridine-2-carboxylic acid N-(carboxymethyl)amide and 3-hydroxypyridine-2-carboxylic acid N-(carboxy-2-hydroxypropyl)amide, being excluded.

3. A compound of the formula I or a physiologically active salt thereof as claimed in claim 1, in which Q is O or S, X is O, Y is $CR^3$, m is 0, A is an unsubstituted $(C_1-C_2)$-alkylene group, B is $CO_2H$ $R^2$ is hydrogen, bromine, chlorine, cyano, $(C_1-C_{18})$-alkyl, $(C_1-C_8)$-alkoxy, $(C_1-C_{18})$-alkoxymethyl, $(C_2-C_{18})$-alkenyloxymethyl, $(C_2-C_{18})$-alkynyloxymethyl, carbamoyl, N-$(C_1-C_{10})$-alkylcarbamoyl, N-$((C_1-C_{12})$-alkoxy-$(C_1-C_4)$-alkyl)carbamoyl, N,N-di-$(C_1-C_8)$-alkylcarbamoyl, N-$(C_3-C_8)$-cycloalkylcarbamoyl, N-$(C_6-C_{12})$-phenylcarbamoyl, N-$(C_7-C_{12})$-phenylalkylcarbamoyl, N-$(C_1-C_6)$-alkyl-N-$(C_6-C_{12})$-phenylcarbamoyl, N-$(C_1-C_6)$-alkyl-N-$(C_7-C_{12})$-phenylalkylcarbamoyl, N-$((C_1-C_6)$-alkoxy-$(C_1-C_6)$alkyl)carbamoyl, carboxyl, $(C_1-C_{20})$-alkoxycarbonyl, $(C_2-C_{20})$-alkenyloxycarbonyl, retinyloxycarbonyl, $(C_3-C_8)$-cycloalkoxycarbonyl, $(C_3-C_8)$-cycloalkyl-$(C_1-C_6)$-alkoxycarbonyl, $(C_3-C_8)$-cycloalkyl-$(C_1-C_6)$-alkoxycarbonyl, phenyl-$(C_1-C_6)$-alkoxycarbonyl, phenoxy-$(C_1-C_6)$-alkoxycarbonyl or benzyloxy-$(C_1-C_6)$-alkoxycarbonyl, where said radicals containing a phenyl radical or moiety may be substituted on said phenyl in the manner defined for $R^1$ and $R^3$ below, one of the radicals $R^1$ or $R^3$ is hydrogen and the other a radical selected from the group hydrogen, fluorine, chlorine, $(C_1-C_8)$-alkyl, $(C_1-C_{10})$-alkoxy, $(C_5-C_6)$-cycloalkyl, $(C_5-C_6)$-cycloalkyl-$(C_1-C_6)$-alkyl, $(C_5-C_6)$-cycloalkyloxy, $(C_5-C_6)$-cycloalkyl-$(C_1-C_6)$-alkoxy, $(C_5-C_{C6})$-cycloalkyloxy-$(C_1-C_6)$-alkyl, $(C_5-C_6)$-cycloalkyloxy-$(C_1-C_6)$-alkoxy, $(C_5-C_6)$-cycloalkyl-$(C_1-C_4)$-alkyl-$(C_1-C_4)$-alkoxy, $(C_5-C_6)$-cycloalkyl-$(C_1-C_4)$-alkoxy-$(C_1-C_2)$ 3 -alkyl, $(C_5-C_6)$-cycloalkoxy-$(C_1-C_4)$-alkoxy-$(C_1-C_2)$-alkyl, —O—$[CH_2]_x$—$C_fH_{(2f+1-g)}F_g$, $(C_1-C_6)$-alkoxy-$(C_1-C_6)$-alkyl, $(C_1-C_6)$-alkoxy-$(C_1-C_6)$-alkoxy, $(C_1-C_6)$-alkoxy-$(C_1-C_4)$-alkoxy-$(C_1-C_2)$-alkyl, $(C_6-C_{12})$-phenoxy, $(C_7-C_{11})$-phenylalkyloxy, $(C_6-C_{12})$-phenoxy-$(C_1-C_6)$-alkoxy or $(C_7-C_{11})$-phenylalkoxy-$(C_1-C_6)$-alkoxy, phenoxy-$(C_1-C_4)$-alkyl, $(C_7-C_{11})$-phenylalkyloxy-$(C_1-C_4)$-alkyl, phenoxy-$(C_1-C_4)$-alkoxy-$(C_1-C_2)$-alkyl and $(C_7-C_{11})$-phenylalkyloxy-$(C_1-C_4)$-alkoxy-$(C_1-C_2)$-alkyl, where said radicals containing an aromatic radical or moiety are substituted on said aromatic radical or moiety by 1, 2, or 3 identical or different substituents selected from the group fluorine, chlorine, cyano, trifluoromethyl, $(C_1-C_{12})$-alkyl, $(C_2-C_{12})$-alkenyl, $(C_2-C_{12})$-alkenyloxy and $(C_1-C_{12})$-alkoxy, and $R^4$ is hydrogen, with 3-hydroxypyridine-2-carboxylic acid N-(carboxymethyl)amide being excluded.

4. A compound of the Formula 1a as claimed in claim 2, in which

Q is O or S,

X is O,

A is an unsubstituted —$CH_2$— group,

B is —$CO_2H$, $R^1$ is hydrogen, $R^{13}$, $R^{15}$ and $R^{16}$ are hydrogen, $R^{14}$ is hydrogen, $(C_1-C_{12})$-alkyl, $(C_2-C_{12})$-alkenyl, chlorine, fluorine, bromine, trifluoromethyl, $(C_1-C_{12})$-alkylsulfonyl, $(C_1-C_{12})$-alkylsulfinyl, phenylsulfonyl, or phenylsulfinyl, where said radical containing a phenyl radical or moiety may be substituted once on said phenyl by fluorine, chlorine or $(C_1-C_5)$-alkoxy, and further wherein $R^{14}$ is $(C_1-C_{10})$-alkoxy, —O—$[CH_2]_x$—$C_fH_{(2f+1-g)}F_g$ or benzyloxy which is optionally substituted once in the phenyl ring by fluorine, chlorine or $(C_1-C_5)$-alkoxy, and $R^4$ is hydrogen, or a physiologically active salt thereof.

5. A compound of the formula I as claimed in claim 1, in which

Q is O,

X is O,

Y is $CR^3$, m is 0,

A is an unsubstituted —$CH_2$— group,

B is $CO_2H$, $R^1$ is hydrogen, $(C_1-C_{10})$-alkoxy, $(C_5-C_6)$-cycloalkyloxy, $(C_5-C_6)$-cycloalkyl-$(C_1-C_2)$-alkoxy, —O—$[CH_2]_x$—$C_fH_{(2f+1-g)}F_g$, $(C_1-C_4)$-alkoxy-$(C_1-C_4)$-alkoxy, phenoxy or benzyloxy where said radicals containing a phenyl radical or moiety are substituted on said phenyl by a substitutent selected from the group fluorine, chlorine, cyano, trifluoromethyl, $(C_1-C_4)$-alkyl and $(C_1-C_4)$-alkoxy, and $R^2$, $R^3$ and $R^4$ are hydrogen, or a physiologically active salt thereof, with 3-hydroxypyridine-2-carboxylic acid N-(carboxymethyl)amide being excluded.

6. A compound of the formula I as claimed in claim 1, in which

Q is S,

X is O,

Y is $CR^3$, m is 0,

A is a —$CH_2$— group,

B is —$CO_2H$, $R^1$ is hydrogen, and $R^2$, $R^3$ and $R^4$ are hydrogen.

7. A compound of the formula I or a physiologically active salt thereof as claimed in claim 1, in which Q is O, X is O, Y is $CR^3$, m is 0

A is an unsubstituted —$CH_2$— group,

B is —$CO_2H$, $R^1$ is hydrogen, and $R^2$ and $R^3$, together with the pyridine carrying them, form a quinoline ring, and $R^4$ is hydrogen.

8. A pharmaceutical composition comprising a compound of the formula I or a physiologically active salt thereof or a prodrug of said compound of formula (I), wherein said prodrug differs from said compound of formula (I), as claimed in claim 1, not excluding 3-hydroxypyridine-2-carboxylic acid N-(carboxymethyl)amide, 3-hydroxypyridine-2-carboxylic acid N-(carboxy-2-hydroxypropyl)amide 3-hydroxypyridine-2-carboxylic acid-N-(glycyl ethyl ester)amide and 3-hydroxypyridine-2-carboxylic acid-N-(threonyl benzyl ester)amide.

9. A compound of the formula (I) or a physiologically active salt thereof as claimed in claim 1, in which the radicals $R^2$ and $R^3$, together with the pyridine carrying them, form a 5, 6, 7, 8-tetrahydroquinoline ring, or $R^2$ and $R^3$ form a carbocyclic or a heterocyclic aromatic ring having 5 or 6 ring atoms.

10. A compound of the formula (I) or a physiologically active salt thereof as claimed in claim 2, wherein $R^1$ or $R^3$, or both $R^1$ and $R^3$, are a radical of the formula D

OZ    (D), where Z is $[CH_2]_v$—$[O]_w$—$[CH_2]_t$—E, wherein E is a $(C_3–C_8)$-cycloalkyl radical and wherein v, w, and t are as defined in claim 2.

11. A compound of the formula (I) or a physiologically active salt thereof as claimed in claim 2, wherein $R^1$ or $R^3$, or both $R^1$ and $R^3$, are a radical of the formula Z, where Z is $[CH_2]_v$—$[O]_w$—$[CH_2]_t$—, wherein E is a $(C_3–C_8)$-cycloalkyl radical and v is not 0 and wherein w and t are as defined in claim 2.

12. A compound of the formula (I) or a physiologically active salt thereof as claimed in claim 2, wherein $R^1$ or $R^3$ or both $R^1$ and $R^3$ are a radical of the formula D:

OZ    (D), in which Z is —$[CH_2]_v$—$[O]_w$—$[CH_2]_t$—E, where E is a phenyl radical of the formula F

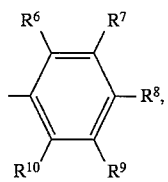

(F)

where v is 0, 1, 2 or 3, w is 0 or 1, and t can be 0 or 1, with the restriction that v is not 0 if w is 1, and in which $R^6$, $R^7$, $R^8$, $R^9$ and $R^{10}$ are identical or different and are hydrogen, fluorine, chlorine, cyano, trifluoromethyl, $(C_1–C_6)$-alkyl, $(C_1–C_6)$-alkoxy, —O—$[CH_2]_x$—$C_fH_{(2f+1-g)}F_g$, N—$(C_1–C_8)$-alkylcarbamoyl, N,N-di-$(C_1–C_8)$-alkylcarbamoyl, N—$(C_3–C_8)$-cycloalkylcarbamoyl or $(C_7–C_{11})$-phenylalkylcarbamoyl, wherein the phenyl of said $(C_7–C_{11})$-phenylalkylcarbamoyl is optionally substituted by fluorine, chlorine, trifluoromethyl or $(C_1–C_6)$-alkoxy.

13. A compound of formula (I) or a physiologically active salt thereof as claimed in claim 2, wherein $R^1$ or $R^3$ or both $R^1$ and $R^3$ are a radical of formula (Z)

—$[CH_2]_v$—$[O]_w$—$[CH_2]_t$—E    (Z)

where E is a phenyl radical of the formula F

(F)

where v is 0, 1, 2 or 3, w is 0 or 1, and t can be 0 or 1, with the restriction that is not 0 if w is 1, and in which $R^6$, $R^7$, $R^8$, $R^9$ and $R^{10}$ are identical or different and are hydrogen, fluorine, chlorine, cyano, trifluoromethyl, $(C_1–C_6)$-alkyl, $(C_1–C_6)$-alkoxy, —O—$[CH_2]_x$—$C_fH_{(2f+1-g)}F_g$, N—$(C_1–C_8)$-alkylcarbamoyl, N,N-di-$(C_1–C_8)$-alkylcarbamoyl, N-$(C_3–C_8)$-cycloalkylcarbamoyl or $(C_7–C_{11})$-phenylalkylcarbamoyl, wherein the phenyl of said $(C_7–C_{11})$-phenylalkylcarbamoyl is optionally substituted by fluorine, chlorine, trifluoromethyl or $(C_1–C_6)$-alkoxy.

14. A compound of the formula (I) or a physiologically active salt thereof as claimed in claim 2, wherein the substituents A and B together are $CH_2COOH$.

15. A prodrug of said compound of the formula (I), wherein said prodrug differs from said compound of formula (I) as claimed in claim 1.

16. A process for preparing compounds according to formula I as claimed in claim 1, in which formula A is a substituted alkylene moiety, B is $CO_2H$, Y is $CR^3$ and m is 0 or 1, by i) reacting either (a) pyridine 2-carboxylic acids of the formula II ($R^{11}$ is H) with the amino esters of the formula III to form the amide esters of the formula IV, or (b) pyridine-2-carboxylic esters of the formula II, wherein $R^1$, $R^2$, $R^3$, Q, and A are as defined in claim 1, $R^{10}$ is $R^4$ or a protecting group, $R^{11}$ is lower alkyl, and $R^{12}$ is H, $(C_1–C_8)$-alkyl or benzyl, under the conditions of aminolysis, to form the compounds of the formula IV;

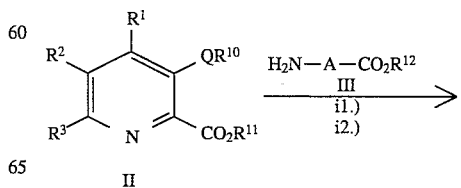

II

-continued

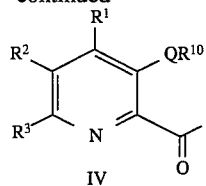

and ii) liberating the compounds of the formulae I and V from their esters of the formula IV;

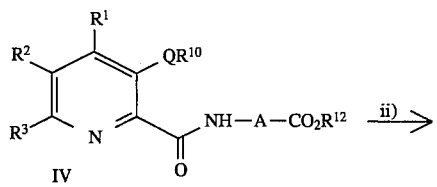

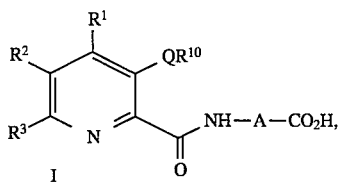

with, where appropriate, iii) the compounds of the formula IV being prepared by alkylation of compounds of the formula V

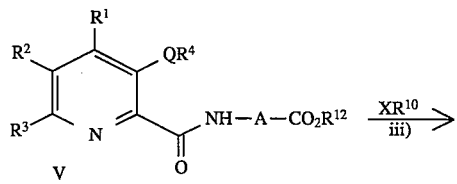

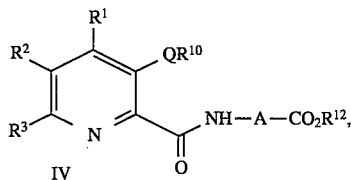

where X is a leaving group, in particular halogen, $OSO_2Me$ or $OSO_2$ phenyl, and, where appropriate, iv) the compounds of the formulae I, V or IV being converted into their pyridine N-oxides (I' or VI)

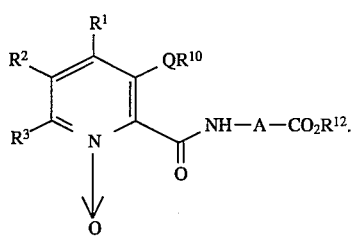

17. A method of inhibiting collagen biosynthesis comprising the step of administering an effective amount of a compound of formula I,

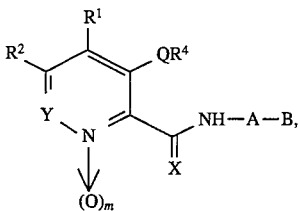

wherein Q, X, Y, m, B, $R^1$, $R^2$, $R^4$, are as defined in claim 1, and A is as defined in claim 18 except that $R^5$ can also be $CH_2SH$, and further wherein the compound of formula I can also be 3-hydroxypyridine-2-carboxylic acid N-(carboxymethyl)amid, 3-hydroxypyridine-2-carboxylic acid-N-(carboxy-2-hydroxypropyl)amide, 3-hydroxypridine-2-carboxylic acid-N-(glycyl ethyl ester)amide and 3-hydroxypyridine-2-carboxylic acid-N-(threonyl benzyl ester)amide, or a physiologically active salt thereof or a prodrug of said compound of formula (I), wherein said prodrug differs from said compound of formula (I), to a patient in recognized need of therapy for a disease involving extracellular collagen deposition.

18. The method of claim 17, wherein said disease is a fibrotic disease of the lung, liver, or skin.

19. A method of inhibiting the action of prolyl-4-hydroxylase in collagen biosynthesis comprising the step of administering an effective amount of a compound of formula I,

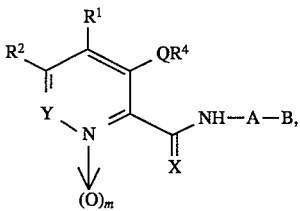

wherein Q, X, Y, m, B, $R^1$, $R^2$, $R^4$, are as defined in claim 1, and A is as defined in claim 18 except that $R^5$ can also be $CH_2SH$, and further wherein the compound of formula I can also be 3-hydroxypyridine-2-carboxylic acid N-(carboxymethyl)amide, 3-hydroxypyridine-2-carboxylic acid N-(carboxy-2-hydroxypropyl)amide, 3-hydroxypyridine-2-carboxylic acid-N-(glycyl ethyl ester)amide and 3-hydroxypyridine-2-carboxylic acid-N-(threonyl benzyl ester)amide, or a physiologically active salt thereof or a prodrug of said compound of formula (I), wherein said prodrug differs from said compound of formula (I), to a patient in recognized need of therapy for a disease involving extracellular collagen deposition.

20. The method of claim 19, wherein said disease is a fibrotic disease of the lung, liver, or skin.

21. A method of fibrosuppression comprising the step of administering an effective amount of a compound of formula I,

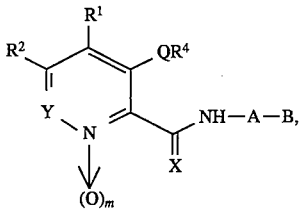

wherein Q, X, Y, m, B, $R^1$, $R^2$, $R^4$, are as defined in claim 1, and A is as defined in claim 18, except that $R^5$ can also be $CH_2SH$, and further wherein the compound of formula I can also be 3-hydroxypyridine-2-carboxylic acid N-(carboxymethyl)amide, 3-hydroxypyridine-2-carboxylic acid N-(carboxy-2-hydroxypropyl)amide, 3-hydroxypyridine-2-carboxylic acid-N-(glycyl ethyl ester)amide and 3-hydroxypyridine-2-carboxylic acid-N-(threonyl benzyl ester)amide, or a physiologically active salt thereof or a prodrug of said compound of formula (I), wherein said prodrug differs from said compound of formula (I), to a patient in recognized need of therapy for a disease involving extracellular collagen deposition.

22. The method of claim 21, wherein said disease is a fibrotic disease of the lung, liver, or skin.

23. A compound of formula I or a physiologically effective salt thereof as claimed in claim 4, wherein Q is O.

24. A compound or physiologically active salt thereof according to claim 12, wherein said radical of formula D is selected from $(C_6-C_{12})$-phenoxy, $(C_7-C_{11})$-phenylalkyloxy, $(C_6-C_{12})$-phenoxy-$(C_1-C_6)$-alkoxy, $(C_7-C_{11})$-phenylalkoxy=$(C_1=C_6)$=alkoxy, $(C_5=C_6)$=cycloalkyloxy, $(C_5=C_6)$=cycloalkyl=$(C_1=C_6)$-alkoxy, $(C_5-C_6)$-cycloalkoxy-$(C_1-C_6)$-alkoxy and $(C_5-C_6)$-cycloalkyl-$(C_1-C_4)$-alkyl-$(C_1-C_4)$-alkoxy.

25. A compound or physiologically active salt thereof according to claim 13, wherein said radical of formula (Z) is selected from phenyl, phenoxy-$(C_1-C_6)$-alkyl, $(C_7-C_{11})$-phenylalkyl, $(C_7-C_{11})$-phenalkyloxy-$(C_1-C_4)$-alkyl, $(C_5-C_6)$-cycloalkyl, $(C_5-C_6)$-cycloalkyl-$(C_1-C_6)$-alkyl, $(C_5-C_6)$-cycloalkoxy-$(C_1-C_4)$-alkyl, $(C_5-C_6)$-cycloalkyl-$(C_1-C_4)$-alkoxy-$C_1-C_2$)-alkyl and $(C_5-C_6)$-cycloalkoxy-$(C_1-C_4)$-alkoxy-$(C_1-C_2)$-alkyl.

26. A method according to claim 17, wherein the substituents A and B of said compound of formula I together are $CH_2COOH$.

27. A method according to claim 19, wherein the substituents A and B of said compound of formula I together are $CH_2COOH$.

28. A method according to claim 21, wherein the substituents A and B of said compound of formula I together are $CH_2COOH$.

* * * * *